(12) United States Patent
Yoo et al.

(10) Patent No.: US 6,583,147 B1
(45) Date of Patent: Jun. 24, 2003

(54) PYRAZOLOPYRIMIDINONE DERIVATIVES FOR THE TREATMENT OF IMPOTENCE

(75) Inventors: Moohi Yoo, Seoul (KR); Wonbae Kim, Seoul (KR); Min Sun Chang, Kyunggi-do (KR); Joong In Lim, Kyunggi-do (KR); Dong Sung Kim, Kyunggi-do (KR); Ik Yon Kim, Kyunggi-do (KR); Tae Kyun Lim, Kyunggi-do (KR); Byoung Ok Ahn, Kyunggi-do (KR); Kyung Koo Kang, Kyunggi-do (KR); Miwon Son, Kyunggi-do (KR); Hyounmie Doh, Seoul (KR); Soonhoe Kim, Kyunggi-do (KR); Hyunjoo Shim, Kyunggi-do (KR); Taeyoung Oh, Kyunggi-do (KR); Heungjae Kim, Kyunggi-do (KR); Dong Goo Kim, Kyunggi-do (KR)

(73) Assignee: Dong A Pharm Co., Ltd., Seoul (KR)

( * ) Notice: Subject to any disclaimer, the term of this patent is extended or adjusted under 35 U.S.C. 154(b) by 0 days.

(21) Appl. No.: 09/831,433

(22) PCT Filed: Nov. 10, 1999

(86) PCT No.: PCT/KR99/00675
§ 371 (c)(1),
(2), (4) Date: May 9, 2001

(87) PCT Pub. No.: WO00/27848
PCT Pub. Date: May 18, 2000

(30) Foreign Application Priority Data

Nov. 11, 1998 (KR) .............................. 98-48100
Apr. 27, 1999 (KR) ........................... 1999-14972
Nov. 9, 1999 (KR) ........................... 1999-49384

(51) Int. Cl.$^7$ ..................... C07D 487/04; A61K 31/519
(52) U.S. Cl. .................................. 514/262.1; 544/262
(58) Field of Search ........................ 544/262; 514/262.1

(56) References Cited

FOREIGN PATENT DOCUMENTS

WO    WO 96/16657    *    6/1996

* cited by examiner

*Primary Examiner*—Richard L. Raymond
*Assistant Examiner*—Hong Liu
(74) *Attorney, Agent, or Firm*—Bachman & LaPointe, P.C.

(57) ABSTRACT

The present invention relates to pyrazolopyrimidinone derivatives of formula 1, their preparation method and pharmaceutical compositions containing the said derivatives. The compounds have efficacy on the treatment of impotence, one of male sexual dysfunctions with the side effects reduced.

10 Claims, No Drawings

PYRAZOLOPYRIMIDINONE DERIVATIVES FOR THE TREATMENT OF IMPOTENCE

BACKGROUND OF THE INVENTION

The present invention relates to pyrazolopyrimidinone derivatives of the following formula 1, their preparation method and pharmaceutical compositions containing the said derivatives. The compounds have efficacy on the treatment of impotence, one of male sexual dysfunctions with the side effects reduced.

FORMULA 1

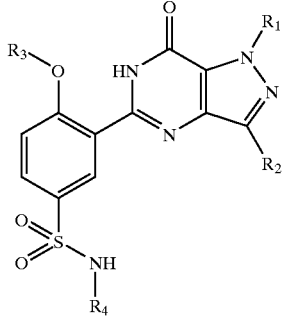

Wherein,
- $R_1$ represents hydrogen, alkyl group of $C_1$–$C_6$, fluoroalkyl group of $C_1$–$C_3$, or cycloalkyl group of $C_3$–$C_6$;
- $R_2$ represents hydrogen, substituted or unsubstituted alkyl group of $C_2$–$C_6$, fluoroalkyl group of $C_1$–$C_3$, or cycloalkyl group of $C_3$–$C_6$;
- $R_3$ represents substituted or unsubstituted alkyl group of $C_1$–$C_6$, fluoroalkyl group of $C_1$–$C_6$, cycloalkyl group of $C_3$–$C_6$, alkenyl group of $C_3$–$C_6$, or alkynyl group of $C_3$–$C_6$; and
- $R_4$ represents substituted or unsubstituted and linear or branched alkyl group of $C_1$–$C_{10}$, substituted or unsubstituted alkenyl group of $C_1$–$C_9$, substituted or unsubstituted cycloalkyl group of $C_3$–$C_6$, substituted or unsubstituted benzene, or substituted or unsubstituted heterocycle selected from the group consisting of pyridine, isoxazole, thiazole, pyrimidine, indan, benzthiazole, pyrazole, thiadiazole, oxazole, piperidine, morpholine, imidazole, pyrrolidine, thienyl, triazole, pyrrole and furyl ring.

In case of $R_2$, $R_3$ and $R_4$ being substituted, the substituent is alkyl group of $C_1$–$C_{10}$, cycloalkyl group of $C_3$–$C_6$, halogen, fluoroalkyl group of $C_1$–$C_6$, alkyloxy group of $C_1$–$C_{10}$, substituted or unsubstituted benzene, or substituted or unsubstituted heterocycle selected from the group consisting of pyridine, isoxazole, thiazole, pyrimidine, indan, benzthiazole, pyrazole, thiadiazole, oxazole, piperidine, morpholine, imidazole, pyrrolidine, thienyl, triazole, pyrrole and furyl ring.

The compounds of formula 1 may exist in tautomeric equilibrium represented by the following reaction scheme 1.

REACTION SCHEME 1

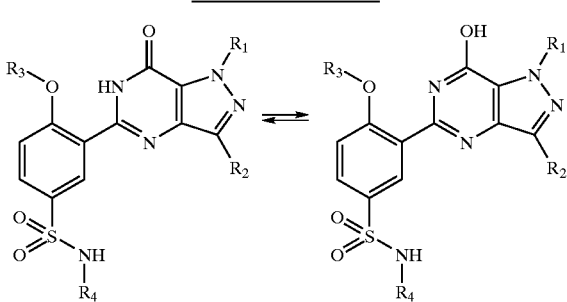

The compounds of formula 1 may contain asymmetric centers and thus they can exist as enantiomers. The present invention includes both mixtures and separate individual isomers.

Male erectile dysfunction is one of the most common sexual dysfunctions in men. Although erectile dysfunction can be primarily psychogenic in origin, it often accompanies chronic illnesses, such as diabetes mellitus, heart disease, hypertension, and a variety of neurological diseases. Its prevalence is strongly related to age, with a estimated prevalence of 2% at age 40 years rising to 25–30% by age of 65. Although no data are available on the prevalence of erectile dysfunction in men aged over 75, it is probably over 50%.

Various treatment options for erectile dysfunction are available, such as counseling, hormonal therapy, self-injection or transurethral application of vasodilator agents, vacuum devices, prosthesis implantation, and venous/arterial surgery. However, these therapeutic options have several limitations such as side effects, high-cost and low efficacy. Therefore it has called for research efforts to develop new, high effective and simple to use treatment methods, potentially oral medication.

Recently, sildenafil has been developed as a therapeutic agent for male erectile dysfunction by oral administration. Sildenafil is the first in a new class of drugs known as inhibiting phosphodiesterase-5 enzyme distributed specifically in corpus cavernosal tissues and induces relaxation of the corpus cavernosal smooth muscle cells, so that blood flow to the penis is enhanced, leading to an erection. Sildenafil has shown a response rate of around 80% in men with erectile dysfunction of organic cause.

On the other hand, U.S. Pat. No. 3,939,161 discloses that 1,3-dimethyl-1H-pyrazolopyrimidinone derivatives exhibit anticonvulsant and sedative activiity, and also exhibit anti-inflammatory activity and gastric antisecretory activity; EP 201,188 discloses that 5-substituted pyrazolopyrimidinone derivatives have effects of antagonizing adenosine receptor and of inhibiting phosphodiesterase enzymes and can be used for the treatment of cardiovascular disorders such as heart failure or cardiac insufficiency; EP 463,756, EP 526,004, WO 93/6,104 and WO 93/7,149 disclose that pyrazolopyrimidinone derivatives which inhibit c-GMP phosphodiesterase more selectively than c-AMP phosphodiesterase have efficacy on cardiovascular disorders such as angina pectoris, hypertension, heart failure, atherosclerosis, chronic asthma, etc.; and WO 94/28,902, WO 96/16,644, WO 94/16,657 and WO 98/49,166 disclose that the known inhibitors of c-GMP phosphodiesterase including the pyrazolopyrimidinone derivatives of the above mentioned patents can be used for the treatment of male erectile dysfunction.

We, the inventors of the present invention, have investigated to develop the improved therapeutic agent for impotence and synthesized new pyrazolo pyrimidinone derivatives which have better potency for the treatment of impotence than that of sildenafil, based on the mechanism of inhibiting phosphodiesterase-5 enzyme. The selectivity over phosphodiesterase-6 distributed in retina and phosphodiesterase-3 distributed in heart, of the compounds of the present invention, is much more improved, to reduce the side effects. The solubility and the metabolism in the liver, which are very important factor affecting the rate of the absorption when administered orally, of the compounds of the present invention is much more improved.

SUMMARY OF THE INVENTION

It is an object of the present invention to provide pyrazolopyrimidinone derivatives represented by formula 1 and their pharmaceutically acceptable salts.

It is another object of the present invention to provide preparation method of the said pyrazolopyrimidinone derivatives.

It is still another object of the present invention to provide pharmaceutical compositions for the treatment of impotence which contain the said pyrazolopyrimidinone derivatives and/or their pharmaceutically acceptable salts as an active ingredient.

DETAILED DESCRIPTION OF THE INVENTION

The present invention provides new pyrazolopyrimidinone derivatives of the following formula 1 and their pharmaceutically acceptable salts.

FORMULA 1

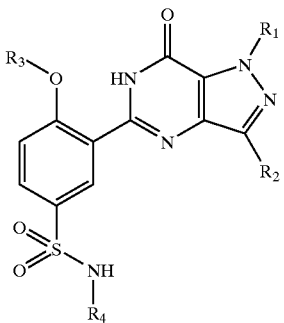

Wherein, $R_1$, represents hydrogen, alkyl group of $C_1$–$C_6$, fluoroalkyl group of $C_1$–$C_3$, or cycloalkyl group of $C_3$–$C_6$;

$R_2$ represents hydrogen, substituted or unsubstituted alkyl group of $C_2$–$C_6$, fluoroalkyl group of $C_1$–$C_3$, or cycloalkyl group of $C_3$–$C_6$;

$R_3$ represents substituted or unsubstituted alkyl group of $C_1$–$C_6$, fluoroalkyl group of $C_1$–$C_6$, cycloalkyl group of $C_3$–$C_6$, alkenyl group of $C_3$–$C_6$, or alkynyl group of $C_3$–$C_6$; and $R_4$ represents substituted or unsubstituted and linear or branched alkyl group of $C_1$–$C_{10}$, substituted or unsubstituted alkenyl group of $C_1$–$C_9$, substituted or unsubstituted cycloalkyl group of $C_3$–$C_6$, substituted or unsubstituted benzene, or substituted or unsubstituted heterocycle selected from the group consisting of pyridine, isoxazole, thiazole, pyrimidine, indan, benzthiazole, pyrazole, thiadiazole, oxazole, piperidine, morpholine, imidazole, pyrrolidine, thienyl, triazole, pyrrole and furyl ring.

In case of $R_2$, $R_3$ and $R_4$ being substituted, the substituent is alkyl group of $C_1$–$C_{10}$, cycloalkyl group of $C_3$–$C_6$, halogen, fluoroalkyl group of $C_1$–$C_6$, alkyloxy group of $C_1$–$C_{10}$, substituted or unsubstituted benzene, or substituted or unsubstituted heterocycle selected from the group consisting of pyridine, isoxazole, thiazole, pyrimidine, indan, benzthiazole, pyrazole, thiadiazole, oxazole, piperidine, morpholine, imidazole, pyrrolidine, thienyl, triazole, pyrrole and furyl ring.

In the formula 1, preferably $R_1$ is alkyl group of $C_1$–$C_3$; $R_2$ is substituted or unsubstituted alkyl group of $C_2$–$C_6$; $R_3$ is substituted or unsubstituted alkyl group of $C_2$–$C_6$; and $R_4$ is substituted or unsubstituted alkyl group of $C_1$–$C_6$, substituted or unsubstituted cycloalkyl group of $C_3$–$C_6$, substituted or unsubstituted benzene, substituted or unsubstituted pyridine, or substituted or unsubstituted pyrrole. In case of $R_2$, $R_3$ and $R_4$ being substituted, the substituent is preferably halogen, substituted or unsubstituted benzene, substituted or unsubstituted heterocycle selected from the group consisting of pyridine, pyrroldine, piperidine, pyrrole, or substituted or unsubstituted cycloalkyl group of $C_3$–$C_6$.

In the formula 1, more preferably $R_4$ is substituted alkyl group of $C_1$–$C_6$, and the substituent is pyrrolidine.

In particular, the preferable compounds of the present invention are:

1) 5-[2-ethoxy-5-(isopropylamidosulfonyl)phenyl]-1-methyl-3-propyl-1,6-dihydro-7H-pyrazolo(4,3-d)pyrimidin-7-one (compound of example 1);

2) 5-[2-ethoxy-5-(benzylamidosulfonyl)phenyl]-1-methyl-3-isobutyl-1,6-dihydro-7H-pyrazolo(4,3-d)pyrimidin-7-one (compound of example 2);

3) 5-[2-propyloxy-5-(isopropylamidosulfonyl)phenyl]-1-methyl-3-propyl-1,6-dihydro-7H-pyrazolo(4,3-d)pyrimidin-7-one (compound of example 3);

4) 5-[2-ethoxy-5-(isopropylamidosulfonyl)phenyl]-1-ethyl-3-propyl-1,6-dihydro-7H-pyrazolo(4,3-d)pyrimidin-7-one (compound of example 5);

5) 5-[2-ethoxy-5-(propylamidosulfonyl)phenyl]-1-methyl-3-propyl-1,6-dihydro-7H-pyrazolo(4,3-d)pyrimidin-7-one (compound of example 7);

6) 5-[2-ethoxy-5-(propylamidosulfonyl)phenyl]-1-ethyl-3-propyl-1,6-dihydro-7H-pyrazolo(4,3-d)pyrimidin-7-one (compound of example 8);

7) 5-[2-ethoxy-5-(butylamidosulfonyl)phenyl]-1-methyl-3-propyl-1,6-dihydro-7H-pyrazolo(4,3-d)pyrimidin-7-one (compound of example 9);

8) 5-[2-ethoxy-5-(2-butylamidosulfonyl)phenyl]-1-methyl-3-propyl-1,6-dihydro-7H-pyrazolo(4,3-d)pyrimidin-7-one (compound of example 10);

9) 5-[2-ethoxy-5-(cyclopropylamidosulfonyl)phenyl]-1-methyl-3-propyl-1,6-dihydro-7H-pyrazolo(4,3-d)pyrimidin-7-one (compound of example 13);

10) 5-[2-ethoxy-5-(cyclopropylamidosulfonyl)phenyl]-1-ethyl-3-propyl-1,6-dihydro-7H-pyrazolo(4,3-d)pyrimidin-7-one (compound of example 14);

11) 5-[2-ethoxy-5-(cyclohexylamidosulfonyl)phenyl]-1-methyl-3-propyl-1,6-dihydro-7H-pyrazolo(4,3-d)pyrimidin-7-one (compound of example 19);

12) 5-[2-ethoxy-5-(benzylamidosulfonyl)phenyl]-1-methyl-3-propyl-1,6-dihydro-7H-pyrazolo(4,3-d)pyrimidin-7-one (compound of example 22);

13) 5-[2-propyloxy-5-(benzylamidosulfonyl)phenyl]-1-methyl-3-propyl-1,6-dihydro-7H-pyrazolo(4,3-d)pyrimidin-7-one (compound of example 23);

14) 5-[2-ethoxy-5-(benzylamidosulfonyl)phenyl]-1-ethyl-3-propyl-1,6-dihydro-7H-pyrazolo(4,3-d)pyrimidin-7-one (compound of example 24);

15) 5-[2-ethoxy-5-(4-fluorophenylamidosulfonyl)phenyl]-1-methyl-3-propyl-1,6-dihydro-7H-pyrazolo(4,3-d)pyrimidin-7-one (compound of example 26);

16) 5-[2-ethoxy-5-(4-t-butylphenylamidosulfonyl)phenyl]-1-methyl-3-propyl-1,6-dihydro-7H-pyrazolo(4,3-d)pyrimidin-7-one (compound of example 28);

17) 5-[2-ethoxy-5-(4-t-butylphenylamidosulfonyl)phenyl]-1-ethyl-3-propyl-1,6-dihydro-7H-pyrazolo(4,3-d)pyrimidin-7-one (compound of example 29);

18) 5-[2-ethoxy-5-(4-isopropylphenylamidosulfonyl)phenyl]-1-methyl-3-propyl-1,6-dihydro-7H-pyrazolo(4,3-d)pyrimidin-7-one (compound of example 31);

19) 5-[2-ethoxy-5-(4-fluorophenylamidosulfonyl)phenyl]-1-ethyl-3-propyl-1,6-dihydro-7H-pyrazolo(4,3-d)pyrimidin-7-one (compound of example 33);

20) 5-[2-ethoxy-5-(4-pyridylamidosulfonyl)phenyl]-1-methyl-3-propyl-1,6-dihydro-7H-pyrazolo(4,3-d)pyrimidin-7-one (compound of example 34);

21) 5-[2-propyloxy-5-(4-pyridylamidosulfonyl)phenyl]-1-methyl-3-propyl-1,6-dihydro-7H-pyrazolo(4,3-d)pyrimidin-7-one (compound of example 35);

22) 5-[2-ethoxy-5-(4-pyridylamidosulfonyl)phenyl]-1-ethyl-3-propyl-1,6-dihydro-7H-pyrazolo(4,3-d)pyrimidin-7-one (compound of example 36);

23) 5-[2-ethoxy-5-(4-pyridylamidosulfonyl)phenyl]-1-methyl-3-isobutyl-1,6-dihydro-7H-pyrazolo(4,3-d)pyrimidin-7-one (compound of example 37);

24) 5-[2-ethoxy-5-(3-pyridylamidosulfonyl)phenyl]-1-methyl-3-propyl-1,6-dihydro-7H-pyrazolo(4,3-d)pyrimidin-7-one (compound of example 38);

25) 5-[2-propyloxy-5-(3-pyridylamidosulfonyl)phenyl)-1-methyl-3-propyl-1,6-dihydro-7H-pyrazolo(4,3-d)pyrimidin-7-one (compound of example 39);

26) 5-[2-ethoxy-5-(3-pyridylamidosulfonyl)phenyl]-1-ethyl-3-propyl-1,6-dihydro-7H-pyrazolo(4,3-d)pyrimidin-7-one (compound of example 40);

27) 5-[2-ethoxy-5-(3-pyridylamidosulfonyl)phenyl]-1-methyl-3-isobutyl-1,6-dihydro-7H-pyrazolo(4,3-d)pyrimidin-7-one (compound of example 41);

28) 5-[2-propyloxy-5-(4-pyridylmethylamidosulfonyl)phenyl]-1-methyl-3-propyl-1,6-dihydro-7H-pyrazolo(4,3-d)pyrimidin-7-one (compound of example 44);

29) 5-[2-ethoxy-5-(4-pyridylmethylamidosulfonyl)phenyl]-1-methyl-3-isobutyl-1,6-dihydro-7H-pyrazolo(4,3-d)pyrimidin-7-one (compound of example 46);

30) 5-[2-ethoxy-5-(3-pyridylmethylamidosulfonyl)phenyl]-1-methyl-3-propyl-1,6-dihydro-7H-pyrazolo(4,3-d)pyrimidin-7-one (compound of example 47);

31) 5-[2-ethoxy-5-(3-pyridylmethylamidosulfonyl)phenyl]-1-methyl-3-isobutyl-1,6-dihydro-7H-pyrazolo(4,3-d)pyrimidin-7-one (compound of example 48);

32) 5-[2-propyloxy-5-(3-pyridylmethylamidosulfonyl)phenyl]-1-methyl-3-propyl-1,6-dihydro-7H-pyrazolo(4,3-d)pyrimidin-7-one (compound of example 49);

33) 5-[2-ethoxy-5-(2-pyridylmethylamidosulfonyl)phenyl]-1-methyl-3-isobutyl-1,6-dihydro-7H-pyrazolo(4,3-d)pyrimidin-7-one (compound of example 51);

34) 5-[2-propyloxy-5-(2-pyridylmethylamidosulfonyl)phenyl]-1-methyl-3-propyl-1,6-dihydro-7H-pyrazolo(4,3-d)pyrimidin-7-one (compound of example 52);

35) 5-[2-propyloxy-5-(1-methyl-3-pyrrolidinylamidosulfonyl)phenyl]-1-methyl-3-propyl-1,6-dihydro-7H-pyrazolo(4,3-d)pyrimidin-7-one (compound of example 53);

36) 5-[2-ethoxy-5-(1-methyl-3-pyrrolidinylamidosulfonyl)phenyl]-1-methyl-3-isobutyl-1,6-dihydro-7H-pyrazolo(4,3-d)pyrimidin-7-one (compound of example 54);

37) 5-[2-propyloxy-5-(1-methyl-2-pyrrolidinylmethylamidosulfonyl)phenyl]-1-methyl-3-propyl-1,6-dihydro-7H-pyrazolo(4,3-d)pyrimidin-7-one (compound of example 56);

38) 5-[2-ethoxy-5-(1-methyl-2-pyrrolidinylmethylamidosulfonyl)phenyl]-1-methyl-3-isobutyl-1,6-dihydro-7H-pyrazolo(4,3-d)pyrimidin-7-one (compound of example 58);

39) 5-[2-propyloxy-5-(1-methyl-3-pyrrolidinylmethylamidosulfonyl)phenyl]-1-methyl-3-propyl-1,6-dihydro-7H-pyrazolo(4,3-d)pyrimidin-7-one (compound of example 60);

40) 5-[2-ethoxy-5-(1-methyl-3-pyrrolidinylmethylamidosulfonyl)phenyl]-1-methyl-3-isobutyl-1,6-dihydro-7H-pyrazolo(4,3-d)pyrimidin-7-one (compound of example 62);

41) 5-[2-propyloxy-5-(1-ethyl-3-pyrrolidinylmethylamidosulfonyl)phenyl]-1-methyl-3-propyl-1,6-dihydro-7H-pyrazolo(4,3-d)pyrimidin-7-one (compound of example 64);

42) 5-[2-ethoxy-5-(1-ethyl-3-pyrrolidinylmethylamidosulfonyl)phenyl]-1-methyl-3-isobutyl-1,6-dihydro-7H-pyrazolo(4,3-d)pyrimidin-7-one (compound of example 66);

43) 5-[2-propyloxy-5-(1-methyl-2-pyrrolidinylethylamidosulfonyl)phenyl]-1-methyl-3-propyl-1,6-dihydro-7H-pyrazolo(4,3-d)pyrimidin-7-one (compound of example 68); and 44) 5-[2-ethoxy-5-(1-methyl-2-pyrrolidinylethylamidosulfonyl)phenyl]-1-methyl-3-isobutyl-1,6-dihydro-7H-pyrazolo(4,3-d)pyrimidin-7-one (compound of example 70).

The compounds of formula 1 according to the present invention can be used in the forms of pharmaceutically acceptable salts, in particular, acid additive salts which are prepared by using pharmaceutically acceptable free acid. Preferred free acids are inorganic acids such as hydrochloric acid, hydrobromic acid, sulfuric acid, phosphoric acid, etc. and organic acids such as citric acid, tartaric acid, acetic acid, lactic acid, maleic acid, fumaric acid, gluconic acid, methanesulfonic acid, glycolic acid, succinic acid, p-toluenesulfonic acid, galacturonic acid, embonic acid, glutamic acid, aspartic acid, etc. Also the compounds of formula 1 can be used in the forms of pharmaceutically acceptable metal salts, particularly alkali metal salts such as sodium or potassium salts.

In addition, the present invention provides preparation methods of pyrazolopyrimidinone derivatives of formula 1, represented by the following reaction scheme 2.

REACTION SCHEME 2

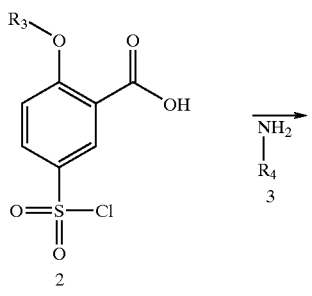

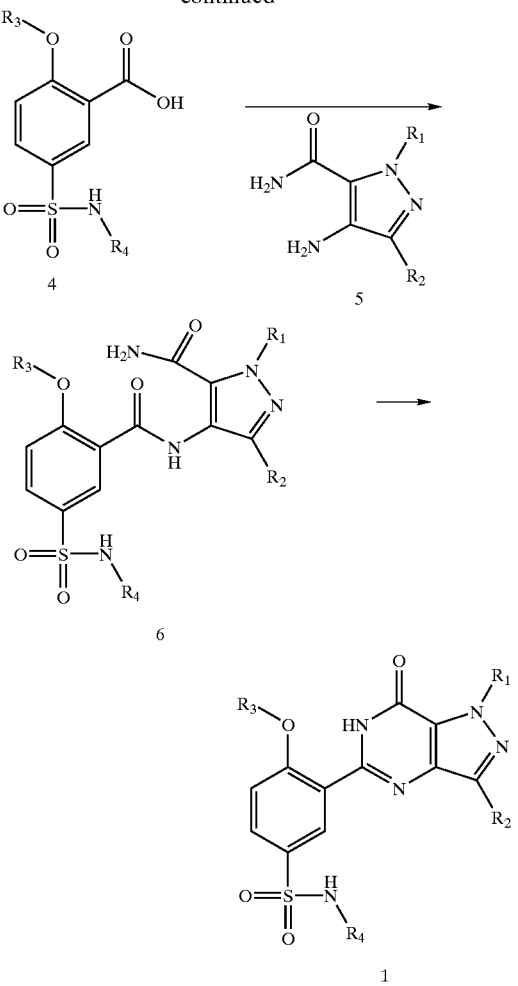

Wherein $R_1$, $R_2$, $R_3$ and $R_4$ are each defined as the formula 1.

The process for preparation according to the present invention comprises the steps of:

1) reacting the chlorosulfonated compound of formula (2) and primary amine (3) under the condition of suitable temperature and suitable solvent to give sulfonamide (4) (step 1):

2) reacting the carboxylic acid (4) prepared in step 1 and pyrazoleamine (5) to give an amide (6) by the known method preparing amide from carboxylic acid and amine (step 2); and 3) cyclizing the amide (6) prepared in step 2 to give the desired compound of formula 1 by the known cyclization method used for preparation of pyrimidinone (step 3).

In step 1, a little excess of 2 equivalents of amine may be used, or a little excess of 1 equivalent of amine and 1 equivalent of acid scavenger such as tertiary amine are may be used together. The reaction temperature is preferred below 20° C.

The known method preparing amide from carboxylic acid and amine in step 2 is the process, for example, in which carboxyl group is transformed into activated acid chloride or acid anhydride by using thionyl chloride, pivaloyl chloride, trichlorobenzoyl chloride, carbonyldiimidazole, diphenylphosphinic chloride, etc. and followed by reacting with amine group, or the process using coupling agents such as DCC (1,3-dicyclo hexylcarbodiimide) or EEDQ (N-ethoxycarbonyl-2-ethoxy-1,3-dihydroquinoline).

The cyclization process in step 3 may be carried out in the presence of a suitable base and a suitable solvent. Preferred bases which are employed in step 3 are metal alkoxides; metal salts of ammonia; amine; hydrides of alkali metal or alkaline earth metal; hydroxides; carbonates; bicarbonates; and bicyclic amidines such as DBU (1,8-diazabicyclo[5.4.0] undec-7-ene) and DBN (1,5-diazabicyclo[4.3.0]non-5-ene). Preferred solvents which are employed in step 3 are alcohols such as methanol, ethanol, isopropanol, t-butanol, etc.; ethers such as tetrahydrofuran, dimethoxyethane, dioxane, etc.; aromatic hydrocarbons such as benzene, toluene, xylene, chlorobenzene, etc.; acetonitrile; dimethylsulfoxide; dimethylformamide; N-methylpyrrolidin-2-one; and pyridine.

In addition, the present invention provides pharmaceutical compositions for the treatment of impotence containing the compounds of formula 1 as an active ingredient.

The present invention provides pharmaceutical formulations which contain, in addition to non-toxic, inert pharmaceutically suitable excipients, one or more compounds according to the present invention, and methods for their preparation.

The compounds of formula 1 according to the present invention can be administered orally or parenterally and be used in general form of pharmaceutical preparation.

The compounds of the present invention can be prepared for oral or parenteral administration by mixing with generally-used fillers, extenders, binders, wetting agents, disintegrating agents, diluents such as surfactants, or excipients.

The present invention also includes pharmaceutical dosage forms in dosage units. This means that the dosage forms are present in the form of individual parts, for example tablets, capsules, pills, suppositories and ampules. The content of the active compound corresponds to a fraction or a multiple of an individual dose. The dosage units can contain, for example, 1, 2, 3 or 4 times or ½, ⅓ or ¼ of the individual dose. An individual dose preferably contains the amount of active compound which is administered in one application and which usually corresponds to a whole, one half, one third or a quarter of a daily dose.

Non-toxic inert pharmaceutically suitable excipients are to be understood as solid, semi-solid or liquid diluents, fillers and formulation auxiliaries of all types.

Preferred pharmaceutical dosage forms which may be mentioned are tablets, capsules, pills, granules, suppositories, solutions, suspensions and emulsions, pastes, ointments, gels, creams, lotions, powders and sprays.

Solid preparations for oral administration are tablets, pill, powders and capsules, liquid preparations for oral administrations are suspensions, solutions, emulsions and syrups, and the above mentioned preparations can contain various excipients such as wetting agents, sweeteners, aromatics and preservatives in addition to generally-used simple diluents such as water and liquid paraffin.

Tablets, capsules, pills and granules can contain the active compound or compounds in addition to the conventional excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption enhancers, for example quaternary ammonium compounds, (g) wetting agents, for example cetyl alcohol and glycerol monostearate, (h) adsorbents, for example kaolin and bentonite, and (i) lubricants, for example talc, calcium stearate, magnesiumstearate, and solid polyethylene glycols, or mixtures of the substances listed under (a) to (i).

The tablets, capsules, pills and granules can be provided with the conventional coatings, and can also be of a composition such that they release the active compound or compounds only or preferentially in a certain part of the intestinal tract, if appropriate in a delayed manner, examples of embedding compositions which can be used being polymeric substances and waxes.

If appropriate, the active compound or compounds can also be present in microencapsulated form with one or more of the above mentioned excipients.

Pharmaceutical dosage forms for parenteral administration are injections, suspensions, emulsions, lyophilized formulations and suppositories.

Suppositories can contain, in addition to the active compound or compounds, the customary water-soluble or water-insoluble excipients, for example polyethylene glycols, fats, for example cacao fat, higher esters (for example $C_{14}$-alcohol with $C_{16}$-fatty acid), witepsol, macrogol, tween 61, laurin fat and glycerol gelatin or mixtures of these substances.

Ointments, pastes, creams and gels can contain, in addition to the active compound or compounds, the customary excipients, for example animal and vegetable fats, waxes, paraffins, starch, tragaanth, cellulose derivatives, polyethylene glycols, silicones, bentonites, silicic acid, talc and zinc oxide, or mixtures of these substances.

Powders and sprays can contain, in addition to the active compound or compounds, the conventioanl excipients, for example lactose, talc, silicic acid, aluminum hydroxide, calcium silicate and polyamide powder, or mixtures of these substances. Sprays can additionally contain the conventional propellants, for example chlorofluorohydrocarbons.

Solutions and emulsions can contain, in addition to the active compound or compounds, the conventioanl excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formalcohol, tetrahydrofurfurylalcohol, polyethyleneglycols and fatty acid esters of sorbitan, or mixtures of these substances.

For parenteral administration, the solutions and emulsions are also be in a sterile form which is isotonic with blood.

Suspensions can contain, in addition to the active compound or compounds, the conventioanl excipients, such as liquid diluents, for example water, ethyl alcohol and propyleneglycol, and suspending agents, for example ethoxylated isostearyl alcohols, polyoxyethylene sorbitol and sorbitan esters, microcrystallinecellulose, aluminummetahydroxide, bentonite, agar-agar, tragacanth and ethyl oleate, or mixtures of these substances.

The pharmaceutical dosage forms mentioned can also contain coloring agents, preservatives and additives which improve the smell and taste, for example peppermint oil and eucalyptus oil, and sweeteners, for example saccharin.

The above mentioned pharmaceutical dosage forms can also contain other pharmaceutically active compounds in addition to the compounds according to the present invention.

The above mentioned pharmaceutical formulations are prepared in the conventioanl method, for example by mixing the active compound or compounds with the excipient or excipients.

The therapeutically active compounds should preferably be present in the abovementioned pharmaceutical dosage forms in a concentration of about 0.1 to 99.5, preferably about 0.5 to 95% by weight of the total mixture.

In general, it has proved advantageous to administer the active compound or compounds according to the present invention in total amounts of about 0.01 to about 100 mg/kg, preferably 0.1 to 30 mg/kg, 1–3 times every 24 hours, if appropriate in the form of several individual doses, to achieve the desired results. However, it may be necessary to properly deviate from the dosages mentioned, and in particular to do so as a function of the nature and body weight of the object to be treated, of the severity of the disease, of the nature of the formulation and of the route of administration of the medicament and the period or interval within which administration takes place.

Thus in some cases it can suffice to manage with less than the abovementioned amount of active compound, while in other cases the abovementioned amount of active compound must be exceeded. The particular optimum dosage and mode of administration required for the active compounds can be determined by any expert on the basis of his expert knowledge.

The pyrazolopyrimidinone derivatives of formula 1 according to the present invention have more prominent efficacy on the treatment of impotence than sildenafil, an already established therapeutic agent for impotence, based on the mechanism of inhibiting phosphodiesterase-5 enzyme. The selectivities for phosphodiesterase-6 and phosphodiesterase-3, of the compounds according to the present invention, are much better than those of sildenafil, reducing the side effects such as visual disorders or cardiovascular disorders. Furthermore, the solubility in water at pH=2 & 5 is much more improved and the metabolism in rat liver is noticeably decreased in some of the pyrazolopyrimidinone derivatives of the present invention. Therefore the probability of better absorption and better in vivo effect can be expected when administered orally compared with sildenafil and the dose of the compound may be reduced.

Practically and presently preferred embodiments of the present invention are illustrative as shown in the following examples.

However, it will be appreciated that those skilled in the art, on consideration of this disclosure, may make modification and improvements within the spirit and scope of the present invention.

The molecular structure of the compounds of formula 1 according to the present invention was identified by IR spectroscopy, UV spectroscopy, NMR spectroscopy, mass spectroscopy and elemental analysis.

EXAMPLES

Example 1

Preparation of 5-[2-Ethoxy-5-(isopropylamidosulfonyl)phenyl]-1-methyl-3-propyl-1,6-dihydro-7H-pyrazolo(4,3-d)pyrimidin-7-one
(Step 1) Preparation of 2-Ethoxy-5-(isopropylamidosulfonyl)benzoic Acid To 1.8 ml of isopropylamine was added 1.9 g of 2-ethoxy-5-chlorosulfonylbenzoic acid in acetone at 0° C., and the mixture was stirred below 20° C. for 3 hours. Acetone was removed by evaporation, the residue was diluted with ethyl acetate and extracted with aqueous saturated sodium bicarbonate solution. The product was re-extracted with ethyl acetate after acidifying the extracted bicarbonate aqueous fraction with HCl. The extracted organic layer was washed with water and saturated brine, dried over anhydrous $MgSO_4$, and concentrated to give 1.95 g of the desired compound.

$NMR(CDCl_3)$: 1.07(d, 6H), 1.58(t, 3H), 3.48(m, 1H), 4.38(q, 2H), 4.50(d, 1H), 7.17(d, 1H), 8.08(dd, 1H), 8.67(d, 1H)

(Step 2) Preparation of 4-[2-ethoxy-5-(isopropylamidosulfonyl)benzamido]-1-methyl-3-propyl-5-carbomoyl Pyrazole To a solution of 1.8 g of 2-ethoxy-5-(isopropylamidosulfonyl)benzoic acid in dichloromethane were added 0.87 ml of triethylamine and 0.98 ml of 2,4,6-trichlorobenzoyl chloride at 0° C., and the mixture was stirred at room temperature for 5 hours. Then to this mixture was added 1-methyl-3-propyl-4-amino-5-carbamoyl pyrazole, and the resulting mixture was stirred. Precipitated crystals were filtered off and the filtrate was diluted with dichloromethane. The organic layer was washed with saturated sodium bicarbonate solution, water and brine in order, dried over anhydrous $MgSO_4$, concentrated and column chromatographed to give 2.0 g of the pure desired compound.

$NMR(CDCl_3)$: 0.90(t, 3H), 1.03(d, 6H), 1.53(t, 3H), 1.59(m, 2H), 2.50(t, 2H), 3.40(m, 1H), 4.00(s,3H), 4.34(q, 2H), 5.27(m, 1H),7.10(d, 1H),7.96(dd, 1H),8.68(d, 1H), 9.23(brs, 1H)

(Step 3) Preparation of 5-[2-Ethoxy-5-(isopropylamidosulfonyl)phenyl]-1-methyl-3-propyl-1,6-dihydro-7H-pyrazolo(4,3-d)pyrimidin-7-one 1.9 g of 4-[2-ethoxy-5-(isopropylamidosulfonyl) benzamido]-1-methyl-3-propyl-5-carbamoyl pyrazole was dissolved in 13.5 ml of t-butanol, to this solution was added 590 mg of potassium t-butoxide, and the mixture was heated to reflux for 20 hours. The reaction mixture was allowed to cool to room temperature, water was added to the mixture, and the conc. HCl was added to adjust the pH to be about 2. The resulting solid was filtered and washed with water. The filtered solid was dissolved in dichloromethane, and the dichloromethane layer was washed with water and brine, dried over anhydrous $MgSO_4$, concentrated and purified by silica gel column chromatography to give 1.15 g of the pure desired compound.

$NMR(CDCl_3)$: 0.99(t, 3H), 1.14(d, 6H),1.61(t, 3H), 1.62 (m, 2H), 2.89(t, 2H), 3.54(m, 1H), 4.25(s,3H), 4.34(q, 2H), 4.57(d, 1H), 7.12(d, 1H), 7.96(dd, 1H), 8.93 (d, 1H), 10.83 (brs,1H)

Example 2

Preparation of 5-[2-Ethoxy-5-(benzylamidosulfonyl) phenyl]-1-methyl-3-isobutyl-1,6-dihydro-7H-pyrazolo(4,3-d)pyrimidin-7-one (Step 1) Preparation of 2-ethoxy-5-(benzylamidosulfonyl) benzoic Acid To 7.4 ml of benzylamine was added 6 g of 2-ethoxy-5-chlorosulfonylbenzoic acid in acetone at 0° C., and the mixture was stirred below 20° C. for 3 hours. Acetone was removed by evaporation, the residue was diluted with dichloromethane and extracted with saturated sodium bicarbonate solution. The product was re-extracted with dichloromethane after acidifying the extracted aqueous bicarbonate layer with HCl. The saturated brine, dried over anhydrous $MgSO_4$, and concentrated to give 5.76 g of the desired compound.

$NMR(CDCl_3)$: 1.58(t, 3H), 4.16(d, 2H), 4.37(q, 2H), 5.01(t, 1H), 7.07(d, 1H), 7.20(m, 5H), 8.00(dd, 1H), 8.60(d, 1H)

(Step 2) Preparation of 4-[2-Ethoxy-5-(benzylamidosulfonyl)benzanido]-1-methyl-3-isobutyl-5-carbamoyl Pyrazole (Method A)To 0.65 g of 2-ethoxy-5-(benzylamidosulfonyl)benzoic acid in dichloromethane was added 0.53 ml of thionyl chloride at 0° C. and the mixture was stirred and refluxed for 3 hours. The mixture was allowed to cool and concentrated (reaction mixture 1). To 0.29 g of 1-methyl-3-isobutyl-4-amino-5-carbamoyl pyrazole in dichloromethane were added 0.27 ml of triethylamine and catalytic amount of dimethylaminopyridine, and the mixture was allowed to cool. The above reaction mixture 1 was added to this mixture. The resulting mixture was stirred in ice bath for 30 min and at room temperature for 1 hour. The mixture was diluted with dichloromethane, washed with 1N HCl, saturated sodium bicarbonate solution, water and brine in order, dried over anhydrous $MgSO_4$ and concentrated to 0.82 g of the desired compound.

(Method B)The mixture of 1.0 g of 2-ethoxy-5-(benzylamidosulfonyl)benzoic acid, 0.59 g of 1-methyl-3-isobutyl-4-amino-5-carbamoyl pyrazole and 0.885 g of EEDQ (2-ethoxy-1-ethoxycarbonyl-1,2-dihydroquinoline) in chloroform was stirred for 3 hours and diluted with chloroform. The organic layer was washed with 1N HCl, saturated sodium bicarbonate solution, water and saturated brine in order, dried over anhydrous $MgSO_4$, concentrated and purified by silica gel column chromatography to 0.92 g of the pure desired compound.

$NMR(CDCl_3)$ 0.97(d, 6H), 1.55(t, 3H), 1.91(m, 1H), 2.40(d, 2H), 3.98(s,3H), 4.11(d, 2H), 4.36(q, 2H), 5.55(t, 1H), 5.94(br s,1H), 7.08(d, 1H), 7.21(m, 5H), 7.58(br s,1H), 7.95(dd, 1H), 8.69(d, 1H), 9.22(br s,1H)

(Step 3) Preparation of 5-[2-Ethoxy-5-(benzylamidosulfonyl)phenyl]-1-methyl-3-isobutyl-1,6-dihydro-7H-pyrazolo(4,3-d)pyrimidin-7-one 0.82 g of 4-[2-ethoxy-5-(benzylamidosulfonyl) benzamido]-1-methyl-3-isobutyl-5-carbamoyl pyrazole was dissolved in ethanol, to this solution was added 0.173 g of sodium methoxide, and the mixture was heated to reflux for 6 hours. The mixture was allowed to cool to room temperature, water was added to the mixture, and the conc. HCl was added to adjust the pH to be about 2. The resulting precipitate was filtered and washed with water. The filtered solid was dissolved in dichloromethane, and the dichloromethane layer was washed with water and brine, dried over anhydrous $MgSO_4$ and concentrated to give 0.775 g of the desired compound.

$NMR(CDCl_3)$: 0.96(d, 6H), 1.62(t, 3H), 2.16(m, 1H), 2.80(d, 2H), 4.18(d, 2H), 4.26(s,3H), 4.35(q, 2H), 4.83(t, 1H), 7.09(d, 1H), 7.22(m, 5H), 7.91(dd, 1H), 8.89 (d, 1H), 10.80(br s,1H)

Examples 3–70

As a starting material, suitable amines corresponding each substituent were employed to prepare the compounds of examples 3–70 by the same method to example 1 or 2.

TABLE 1

| example | $R_1$ | $R_2$ | $R_3$ | $R_4$ |
|---------|-------|-------|-------|-------|
|         | NMR data (solvent:$CDCl_3$ if not specified) | | | |
| 3 | methyl | propyl | propyl | 2-propyl |
|   | 1.00(t, 3H), 1.14(d, 6H), 1.16(t, 3H), 1.83(m, 2H), 2.06(m, 2H), 2.93(t, 2H), 3.53(m, 1H), 4.24(t, 2H), 4.25(s, 3H), 4.39(d, 1H), 7.15(d, 1H), 7.97(dd, 1H), 8.94(d, 1H), 10.90(br s, 1H) | | | |

TABLE 1-continued

| example | R₁ | R₂ | R₃ | R₄ |
|---|---|---|---|---|
| | NMR data (solvent:CDCl₃ if not specified) | | | |
| 4 | methyl | isobutyl | ethyl | 2-propyl |
| | 0.97(d, 6H), 1.14(d, 6H), 1.63(t, 3H), 2.20(m, 1H), 2.81(d, 2H), 3.55(m, 1H), 4.26(s, 3H), 4.35(q, 2H), 7.11(d, 1H), 7.95(dd, 1H), 8.92(d, 1H), 10.85(br s, 1H) | | | |
| 5 | ethyl | propyl | ethyl | 2-propyl |
| | 1.00(t, 3H), 1.14(d, 6H), 1.49(t, 3H), 1.63(t, 3H), 1.84(m, 2H), 2.92(t, 2H), 3.57(m, 1H), 4.35(q, 2H), 4.35(q, 2H), 4.35(d, 1H), 7.11(d, 1H), 7.94(dd, 1H), 8.94(d, 1H), 10.85(br s, 1H) | | | |
| 6 | methyl | propyl | ethyl | methyl |
| | 1.00(t, 3H), 1.62(t, 3H), 1.83(m, 2H), 2.70(d, 3H), 2.90(t, 2H), 4.25(s, 3H), 4.35(q, 2H), 4.50(q, 1H), 7.12(d, 1H), 7.93(dd, 1H), 8.89(d, 1H), 10.8(br s, 1H) | | | |
| 7 | methyl | propyl | ethyl | propyl |
| | 0.88(t, 3H), 1.00(t, 3H), 1.50(m, 2H), 1.61(t, 3H), 1.82(m, 2H), 2.94(m, 4H), 4.25(s, 3H), 4.33(q, 2H), 4.50(t, 1H), 7.11(d, 1H), 7.92(dd, 1H), 8.89(d, 1H), 10.82(br s, 1H) | | | |
| 8 | ethyl | propyl | ethyl | propyl |
| | 0.89(t, 3H), 1.01(t, 3H), 1.50(t, 3H), 1.53(m, 2H), 1.63(t, 3H), 1.83(m, 2H), 2.94(m, 4H), 4.35(q, 2H), 4.40(t, 1H), 4.62(q, 2H), 7.12(d, 1H), 7.91(dd, 1H), 8.92(d, 1H), 10.82(br s, 1H) | | | |
| 9 | methyl | propyl | ethyl | butyl |
| | 0.88(t, 3H), 1.00(t, 3H), 1.30(m, 2H), 1.44(m, 2H), 1.62(t, 3H), 1.83 (m, 2H), 2.94(m, 4H), 4.25(s, 3H), 4.40 (q, 2H), 4.50(t, 1H), 7.11(d, 1H), 7.93(dd, 1H), 8.89(d, 1H), 11.1(br s, 1H) | | | |
| 10 | methyl | propyl | ethyl | 2-butyl |
| | 0.84(t, 3H), 1.00(t, 3H), 1.09(d, 3H), 1.42(m, 2H), 1.63(t, 3H), 2.91(t, 2H), 3.32(m, 1H), 4.26(s, 3H), 4.35(q, 2H), 7.10(d, 1H), 7.98(dd, 1H), 8.94(d, 1H) | | | |
| 11 | methyl | propyl | ethyl | 3-pentyl |
| | 0.78(t, 6H), 1.00(t, 3H), 1.50(m, 4H), 1.62(t, 3H), 1.87(m, 2H), 2.90(t, 2H), 3.20(m, 1H), 4.25(s, 3H), 4.35(q, 2H), 7.12(d, 1H), 7.98(dd, 1H), 8.92(d, 1H), 10.83(br s, 1H) | | | |
| 12 | methyl | propyl | ethyl | t-butyl |
| | 1.00(t, 3H), 1.27(s, 9H), 1.62(t, 3H), 1.84(m, 2H), 2.90(t, 2H), 4.25(s, 3H), 4.34(q, 2H), 4.60(s, 3H), 7.10(d, 1H), 7.96(dd, 1H), 8.96(d, 1H) | | | |
| 13 | methyl | propyl | ethyl | cyclopropyl |
| | 0.65(m, 4H), 1.00(t, 3H), 1.62(t, 3H), 1.81(m, 2H), 2.32(m, 1H), 2.90(t, 2H), 4.25(s, 3H), 4.38(q, 2H), 7.13(d, 1H), 7.96(dd, 1H), 8.93(d, 1H), 10.83(br s, 1H) | | | |
| 14 | ethyl | propyl | ethyl | cyclopropyl |
| | 0.65(m, 4H), 1.00(t, 3H), 1.49(4, 3H), 1.63(t, 3H), 1.84(m, 2H), 2.30(m, 1H), 2.92(t, 2H), 4.36(q, 2H), 4.62(q, 2H), 4.89(br s, 1H), 7.14(d, 1H), 7.97(dd, 1H), 8.96(d, 1H), 10.82(br s, 1H) | | | |
| 15 | methyl | isobutyl | ethyl | cyclopropyl |
| | 0.65(m, 4H), 0.97(d, 6H), 1.63(t, 3H), 2.18(m, 1H), 2.31(m, 1H), 2.81(d, 2H), 4.27(s, 3H), 4.36(q, 2H), 4.88(br s, 1H), 7.13(d, 1H), 7.97(dd, 1H), 8.95(d, 1H), 10.82(br s, 1H) | | | |
| 16 | methyl | propyl | propyl | cyclopropyl |
| | 0.65(m, 4H), 1.00(t, 3H), 1.17(t, 3H), 1.84(m, 2H), 2.04(m, 2H), 2.32(m, 1H), 2.92(t, 2H), 4.25(s, 3H), 4.25(t, 2H), 4.90(br s, 1H), 7.15(d, 1H), 7.98(dd, 1H), 9.00(d, 1H), 10.84(br s, 1H) | | | |
| 17 | methyl | propyl | ethyl | cyclobutyl |
| | 0.65(m, 4H), 1.00(t, 3H), 1.17(t, 3H), 1.84(m, 2H), 2.04(m, 2H), 2.32(m, 1H), 2.92(t, 2H), 4.25(s, 3H), 4.25(t, 2H), 4.90(br s, 1H), 7.15(d, 1H), 7.98(dd, 1H), 9.00(d, 1H), 10.84(br s, 1H) | | | |
| 18 | methyl | propyl | ethyl | cyclopentyl |
| | 1.00(t, 3H), 1.56–1.82(m, 10H), 1.62(t, 3H), 2.91(t, 2H), 3.68(m, 1H), 4.25(s, 3H), 4.40(q, 2H), 4.45(d, 1H), 7.11(d, 1H), 7.94(dd, 1H), 8.92(d, 1H), 10.83(br s, 1H) | | | |
| 19 | methyl | propyl | ethyl | cyclohexyl |
| | 1.00(t, 3H), 1.19(m, 4H), 1.61(t, 3H), 1.61(m, 4H), 1.84(m, 4H), 2.90(t, 2H), 3.23(m, 1H), 4.25(s, 3H), 4.35(q, 2H), 4.54(d, 2H), 7.09(d, 1H), 7.94(dd, 1H), 8.91(d, 1H), 10.85(br s, 1H) | | | |
| 20 | methyl | isobutyl | ethyl | cyclohexyl |
| | 0.97(d, 6H), 1.21(m, 6H), 1.62(t, 3H), 1.61(m, 2H), 1.82(m, 2H), 2.19(m, 1H), 2.80(d, 2H), 3.20(m, 1H), 4.26(s, 3H), 4.35(q, 2H), 4.50(d, 1H), 7.10(d, 1H), 7.97(dd, 1H), 8.91(d, 1H), 10.82(br s, 1H) | | | |
| 21 | methyl | propyl | ethyl | 2-tetrafuranylmethyl |
| | 1.01(t, 3H), 1.62(t, 3H), 1.84(m, 6H), 2.92(t, 2H), 2.97(m, 1H), 3.22(m, 1H), 3.73(m, 2H), 4.00(m, 1H), 4.26(s, 3H), 4.35(q, 2H), 4.87(m, 1H), 7.12(d, 1H), 7.91(dd, 1H), 8.90(d, 1H), 10.83(br s, 1H) | | | |
| 22 | methyl | propyl | ethyl | benzyl |
| | 1.00(t, 3H), 1.63(t, 3H), 1.85(m, 2H), 2.91(t, 2H), 4.18(d, 2H), 4.26(s, 3H), 4.37(q, 2H), 4.82(t, 1H), 7.09(d, 1H), 7.23(m, 5H), 7.92(dd, 1H), 8.90(d, 1H) | | | |
| 23 | methyl | propyl | propyl | benzyl |
| | 1.00(t, 3H), 1.16(t, 3H), 1.63(t, 2H), 2.00(m, 2H), 2.91(t, 2H), 4.20(m, 4H), 4.24(s, 3H), 4.81(t, 1H), 7.10(d, 1H), 7.22(m, 5H), 7.96(dd, 1H), 8.92(d, 1H), 10.84(br s, 1H) | | | |
| 24 | ethyl | propyl | ethyl | benzyl |
| | 1.00(t, 3H), 1.50(t, 3H), 1.63(t, 3H), 1.84(m, 2H), 2.93(t, 2H), 4.18(d, 2H), 4.36(q, 2H), 4.60(q, 2H), 4.65(t, 1H), 7.10(d, 1H), 7.24(m, 5H), 7.94(dd, 1H), 8.92(d, 1H), 10.81(br s, 1H) | | | |
| 25 | methyl | propyl | ethyl | phenyl |
| | 1.02(t, 3H), 1.57(t, 3H), 1.63(t, 2H), 2.90(t, 2H), 4.25(s, 3H), 4.28(q, 2H), 6.70(s, 1H), 7.00(d, 1H), 7.12(m, 5H), 7.74(dd, 1H), 8.86(d, 1H) | | | |
| 26 | methyl | propyl | ethyl | 4-fluorophenyl |
| | 1.00(t, 3H), 1.59(t, 3H), 1.81(m, 2H), 2.87(t, 2H), 4.25(s, 3H), 4.30(q, 2H), 6.79(s, 1H), 6.98(m, 5H), 7.70(dd, 1H), 8.80(d, 1H), 10.80(br s, 1H) | | | |
| 27 | methyl | propyl | ethyl | 4-tolyl |
| | 1.03(t, 3H), 1.59(t, 3H), 1.64(m, 2H), 2.25(s, 3H), 2.91(t, 2H), 4.25(s, 3H), 4.30(q, 2H), 6.52(s, 1H), 6.99(m, 5H), 7.74(dd, 1H), 8.87(d, 1H) | | | |
| 28 | methyl | propyl | ethyl | 4-t-butylphenyl |
| | 1.01(t, 3H), 1.21(s, 9H), 1.59(t, 3H), 1.63(m, 2H), 2.90(t, 2H), 4.25(s, 3H), 4.30(q, 2H), 6.70(s, 1H), 7.00(m, 3H), 7.24(d, 2H), 7.73(dd, 1H), 8.90(d, 1H), 10.80(br s, 1H) | | | |
| 29 | ethyl | propyl | ethyl | 4-t-butylphenyl |
| | 1.02(t, 3H), 1.21(s, 9H), 1.48(t, 3H), 1.59(t, 3H), 1.83(m, 2H), 2.92(t, 2H), 4.30(q, 2H), 4.61(q, 2H), 6.62(br s, 1H), 7.02(m, 3H), 7.24(d, 2H), 7.75(dd, 1H), 8.91(d, 1H), 10.80(br s, 1H) | | | |
| 30 | methyl | isobutyl | ethyl | 4-t-butylphenyl |
| | 0.99(d, 6H), 1.21(s, 9H), 1.58(t, 3H), 2.00(m, 1H), 2.81(d, 2H), 4.26(s, 3H), 4.30(q, 2H), 6.57(br s, 1H), 7.00(m, 3H), 7.24(d, 2H), 7.78(dd, 1H), 8.96(d, 1H), 10.80(br s, 1H) | | | |
| 31 | methyl | propyl | ethyl | 4-isopropylphenyl |
| | 1.02(t, 3H), 1.14(d, 6H), 1.57(t, 3H), 1.66(m, 2H), 2.80(m, 1H), 2.90(t, 2H), 4.25(s, 3H), 4.32(q, 2H), 6.59(s, 1H), 7.02(m, 5H), 7.73(dd, 1H), 8.89(d, 1H), 10.80(br s, 1H) | | | |

TABLE 1-continued

| example | R₁ | R₂ | R₃ | R₄ NMR data (solvent:CDCl₃ if not specified) |
|---|---|---|---|---|
| 32 | methyl | propyl | ethyl | 3,5-dimethylphenyl 1.01(t, 3H), 1.59(t, 3H), 1.64(m, 2H), 2.20(s, 6H), 2.90(t, 2H), 4.25(s, 3H), 4.30 (q, 2H), 6.55 (s, 1H), 6.72 (s, 3H) 7.01(d, 1H), 7.78(dd, 1H), 8.89(d, 1H), 10.78(br s, 1H) |
| 33 | ethyl | propyl | ethyl | 4-fluorophenyl 1.00(t, 3H), 1.49(t, 3H), 1.61(t, 3H), 1.80(m, 2H), 2.89(t, 2H), 4.30(q, 2H), 4.61(q, 2H), 6.72(s, 1H), 7.04(m, 5H), 7.68(dd, 1H), 8.80(d, 1H), 10.79(br s, 1H) |
| 34 | methyl | propyl | ethyl | 4-pyridyl (DMSO-d⁶) 0.97(t, 3H), 1.31(t, 3H), 1.72(m, 2H), 2.78(t, 2H), 4.10(q, 2H), 4.12(q, 2H), 6.94(d, 2H), 7.22(d, 1H), 7.86(dd, 1H), 7.99(m, 3H), 12.10(br s, 1H) |
| 35 | methyl | propyl | propyl | 4-pyridyl (DMSO-d⁶) 0.92(t, 6H), 1.71(m, 4H), 2.76(t, 2H), 4.01(t, 2H), 4.13(s, 3H), 6.93(d, 2H), 7.23(d, 1H), 7.87(d, 1H), 7.98(m, 3H), 12.05(br s, 1H) |
| 36 | ethyl | propyl | ethyl | 4-pyridyl (DMSO-d⁶) 9.93(t, 3H), 1.31(t, 3H), 1.38(t, 3H), 1.72(m, 2H), 2.78(t, 2H), 4.14(q, 2H), 4.51(q, 2H), 6.93(d, 2H), 7.22(d, 1H), 7.88(dd, 1H), 7.97(m, 3H), 12.10(br s, 1H) |
| 37 | methyl | isobutyl | ethyl | 4-pyridyl (DMSO-d⁶) 0.90(d, 6H), 1.30(t, 3H), 2.08(m, 1H), 2.66(d, 2H), 4.13(q, 2H), 4.15(s, 3H), 6.92(d, 2H), 7.21(d, 1H), 7.87(dd, 1H), 7.94(d, 1H), 8.00(d, 2H), 12.10(br s, 1H) |
| 38 | methyl | propyl | ethyl | 3-pyridyl (DMSO-d⁶) 0.94(t, 3H), 1.29(t, 3H), 1.72(m, 2H), 2.77(t, 2H), 4.15(s, 3H), 4.15(q, 2H), 7.30(m, 2H), 7.54(d, 1H), 7.64(dd, 1H), 7.96(d, 1H), 8.25(d, 2H), 8.30(s, 1H), 10.56(br s, 1H), 12.13(br s, 1H) |
| 39 | methyl | propyl | propyl | 3-pyridyl (DMSO-d⁶) 0.91(t, 3H), 0.93(t, 3H), 1.72(m, 4H), 2.76(t, 2H), 4.04(t, 2H), 4.14(s, 3H), 7.28(m, 2H), 7.54(m, 1H), 7.82(dd, 1H), 7.95(m, 1H), 8.25(d, 1H), 8.29(d, 1H), 10.55(br s, 1H), 12.08(br s, 1H) |
| 40 | ethyl | propyl | ethyl | 3-pyridyl (DMSO-d⁶) 0.94(t, 3H), 1.29(t, 3H), 1.38(t, 3H), 1.75(m, 2H), 2.80(t, 2H), 4.14(q, 2H), 4.53(q, 2H), 7.27(m, 2H), 7.54(d, 1H), 7.83(dd, 1H), 7.96(m, 1H), 8.28(d, 2H), 8.30(s, 1H), 10.56(br s, 1H), 12.13(br s, 1H) |
| 41 | methyl | isobutyl | ethyl | 3-pyridyl (DMSO-d⁶) 0.91(d, 6H), 1.29(t, 3H), 2.10(m, 1H), 2.66(d, 2H), 4.12(q, 2H), 4.14(s, 3H), 7.28(m, 2H), 7.54(d, 1H), 7.84(dd, 1H), 7.94(d, 1H), 8.25(d, 2H), 8.29(d, 1H), 10.56(br s, 1H), 12.12(br s, 1H) |
| 42 | methyl | propyl | ethyl | 2-pyridyl (DMSO-d⁶) 0.96(t, 3H), 1.32(t, 3H), 1.75(m, 2H), 2.78(t, 2H), 4.15(s, 3H), 4.15(q, 2H), 6.88(m, 1H), 7.18(d, 1H), 7.27(dd, 1H), 7.73(m, 1H), 8.01(m, 3H), 12.10(br s, 1H) |
| 43 | methyl | propyl | ethyl | 4-pyridylmethyl 0.99(t, 3H), 1.62(t, 3H), 1.80(m, 2H), 2.89(t, 2H), 4.23(q, 2H), 4.25(s, 3H), 4.33(q, 2H), 5.19(t, 1H), 7.08(d, 1H), 7.18(d, 2H), 7.89(dd, 1H), 8.48(dd, 2H), 8.89(d, 1H), 10.80(br s, 1H) |
| 44 | methyl | propyl | propyl | 4-pyridylmethyl 0.99(t, 3H), 1.16(t, 3H), 1.62(m, 2H), 2.00(m, 2H), 2.90(t, 2H), 4.21(d, 2H), 4.25(s, 3H), 4.25(q, 2H), 5.20(t, 1H), 7.09(d, 1H), 7.18(d, 2H), 7.89(dd, 1H), 8.48(m, 2H), 8.90(d, 1H), 10.82(br s, 1H) |
| 45 | ethyl | propyl | ethyl | 4-pyridylmethyl (DMSO-d⁶) 0.92(t, 3H), 1.35(m, 6H), 1.73(m, 2H), 2.78(t, 2H), 4.03(s, 2H), 4.18(q, 2H), 4.52(q, 2H), 7.28(m, 3H), 7.87(m, 1H), 7.98(m, 1H), 8.45(m, 2H) |
| 46 | methyl | isobutyl | ethyl | 4-pyridylmethyl 0.97(d, 6H), 1.62(t, 3H), 2.18(m, 1H), 2.80(d, 2H), 4.22(d, 2H), 4.26(s, 3H), 4.35(q, 2H), 7.08(d, 1H), 7.22(d, 2H), 7.89(dd, 1H), 8.48(m, 2H), 8.89(d, 1H), 10.80(br s, 1H) |
| 47 | methyl | propyl | ethyl | 3-pyridylmethyl (DMSO-d⁶) 0.93(t, 3H), 1.33(t, 3H), 1.74(m, 2H), 2.78(t, 2H), 4.02(s, 2H), 4.17(s, 3H), 4.19(q, 2H), 7.31(m, 2H), 7.63(m, 1H), 7.88(dd, 1H), 7.97(d, 1H), 8.42(m, 2H), 11.82(br s, 1H) |
| 48 | methyl | isobutyl | ethyl | 3-pyridylmethyl 0.94(d, 6H), 1.60(t, 3H), 2.17(m, 1H), 2.77(d, 2H), 4.20(d, 2H), 4.25(s, 3H), 4.30(q, 2H), 5.42(m, 1H), 7.08(d, 1H), 7.21(dd, 1H), 7.64(m, 1H), 7.89(dd, 1H), 8.37(d, 1H), 8.44(dd, 1H), 8.84(d, 1H), 40.82(br s, 1H) |
| 49 | methyl | propyl | propyl | 3-pyridylmethyl 0.98(t, 3H), 1.17(t, 3H), 1.79(m, 2H), 1.98(m, 2H), 2.89(t, 2H), 4.23(t, 2H), 4.23(d, 2H), 4.25(s, 3H), 5.14(t, 1H), 7.10(d, 1H), 7.19(m, 1H), 7.65(d, 1H), 7.90(dd, 1H), 8.38(s, 1H), 8.45(d, 1H), 8.88(d, 1H), 10.85(br s, 1H) |
| 50 | methyl | propyl | ethyl | 2-pyridylmethyl 1.01(t, 3H), 1.59(t, 3H), 1.84(m, 2H), 2.92(t, 2H), 4.29(s, 3H), 4.32(q, 2H), 6.03(br s, 1H), 7.09(m, 3H), 7.54(m, 1H), 7.91(dd, 1H), 8.40(d, 1H), 8.87(d, 1H) |
| 51 | methyl | isobutyl | ethyl | 2-pyridylmethyl 0.98(d, 6H), 1.59(t, 3H), 2.20(m, 1H), 2.82(d, 2H), 4.25(s, 3H), 4.31(q, 2H), 4.29(d, 2H), 7.12(m, 3H), 7.56(m, 1H), 7.91(dd, 1H), 8.40(d, 1H), 8.87(d, 1H) |
| 52 | methyl | propyl | propyl | 2-pyridylmethyl 1.01(t, 3H), 1.14(t, 3H), 1.84(m, 2H), 2.01(m, 2H), 2.93(t, 2H), 4.20(t, 2H), 4.25(s, 3H), 4.29(d, 2H), 5.98(t, 1H), 7.06(d, 1H), 7.15(m, 2H), 7.56(m, 1H), 7.91(dd, 1H), 8.40(m, 1H), 8.89(d, 1H), 10.82(br s, 1H) |
| 53 | methyl | propyl | propyl | 1-methyl-3-pyrrolidinyl 1.00(t, 3H), 1.16(t, 3H), 1.85(m, 4H), 2.04(m, 2H), 2.12(m, 2H), 2.40(m, 1H), 2.51(m, 1H), 2.77(m, 1H), 2.91(t, 2H), 3.95(m, 1H), 4.23(q, 2H), 4.25(s, 3H), 7.11(d, 1H), 7.92(dd, 1H), 8.89(d, 1H) |
| 54 | methyl | isobutyl | ethyl | 1-methyl-3-pyrrolidinyl 0.97(d, 6H), 1.62(t, 3H), 1.80(m, 2H), 2.15(m, 3H), 2.25(s, 3H), 2.38(m, 1H), 2.52(m, 1H), 2.75(m, 1H), 2.81(d, 2H), 3.93(m, 1H), 4.26(s, 3H), 4.35(q, 2H), 7.10(d, 1H), 7.94(dd, 1H), 8.88(d, 1H) |
| 55 | methyl | propyl | ethyl | 1-methyl-2-pyrrolidinyl methyl 1.02(t, 3H), 1.63(t, 3H), 1.80(m, 2H), 1.86(m, 2H), 2.20(m, 4H), 2.94(t, 2H), 2.99(s, 3H), 3.38(m, 1H), 3.60(m, 2H), 3.83(m, 1H), 4.27(s, 3H), 4.36(q, 2H), 7.18(d, 1H), 8.00(dd, 1H), 8.88(d, 1H) |
| 56 | methyl | propyl | ethyl | 1-methyl-2-pyrrolidinyl methyl 0.92(t, 3H), 1.05(t, 3H), 1.60(m, 3H), 1.75(m, 3H), 1.92(m, 2H), 2.06(s, 3H), 2.18(m, 1H), 2.30(m, 1H), 2.82(t, 2H), 2.90(m, 1H), 4.13(q, 2H), 4.16(s, 3H), 7.03(d, 1H), 7.85(dd, 1H), 8.82(d,.1H) |
| 57 | ethyl | propyl | ethyl | 1-methyl-2-pyrrolidinyl methyl 1.01(t, 3H), 1.49(t, 3H), 1.63(t, 3H), 1.71(m, 4H), 1.84(m, 2H), 2.16(s, 3H), 2.21(m, 1H), 2.31 (m, 1H), 2.93(t, 2H), 3.03(m, 3H), 4.35(q, 2H), 4.60 (q, 2H), 7.12(d, 1H), 7.94(dd, 1H), 8.92(d, 1H) |
| 58 | methyl | isobutyl | ethyl | 1-methyl-2-pyrrolidinyl methyl 1.00(d, 6H), 1.64(t, 3H), 1.72(m, 4H), 2.18(s, 3H), 2.20(m, 1H), 2.44(m, 1H), 2.83(d, 2H), 3.06(m, 3H), 4.28(s, 3H), 4.38(q, 2H), 7.13(d, 1H), 7.94(dd, 1H), 8.91(d, 1H) |
| 59 | methyl | propyl | ethyl | 1-methyl-3-pyrrolidinyl methyl 0.99(t, 3H), 1.50(m, 1H), 1.60(t, 3H), 1.83(m, 2H), 1.95(m, 1H), 2.22(m, 2H), 2.28(s, 3H), |

TABLE 1-continued

| example | R₁ | R₂ | R₃ | R₄ | NMR data (solvent:CDCl₃ if not specified) |
|---|---|---|---|---|---|
| | | | | | 2.75(m, 1H), 2.88(t, 2H), 2.97(d, 1H), 3.65(m, 1H), 4.24(s, 3H), 4.29(q, 2H), 7.09(d, 1H), 7.90(dd, 1H), 8.82(d, 1H) |
| 60 | methyl | propyl | propyl | 1-methyl-3-pyrrolidinyl methyl | 0.98(t, 3H), 1.15(t, 3H), 1.45(m, 1H), 1.80(m, 2H), 2.00(m, 3H), 2.20(m, 2H), 2.25(s, 3H), 2.34(m, 2H), 2.70(m, 1H), 2.86(t, 2H), 2.95(d, 2H), 3.62(t, 1H), 4.20(q, 2H), 4.23(s, 3H), 7.09(d, 1H), 7.88(dd, 1H), 8.81(d, 1H) |
| 61 | ethyl | propyl | ethyl | 1-methyl-3-pyrrolidinyl methyl | 1.00(t, 3H), 1.50(t, 3H), 1.50(m, 1H), 1.62(t, 3H), 1.84(d, 2H), 2.00(m, 1H), 2.20(m, 1H), 2.29(s, 3H), 2.37(m, 3H), 2.80(m, 1H), 2.90(t, 2H), 2.99(d, 2H), 4.34(q, 2H), 4.61(q, 2H), 7.10(d, 1H), 7.94(dd, 1H), 8.87(d, 1H) |
| 62 | methyl | isobutyl | ethyl | 1-methyl-3-pyrrolidinyl methyl | 0.94(d, 6H), 1.50(m, 1H), 1.57(t, 3H), 1.95(m, 1H), 2.15(m, 2H), 2.24(s, 3H), 2.33(m, 3H), 2.70(m, 1H), 2.75(d, 2H), 2.95(d, 2H), 3.61(m, 1H), 4.27(s, 3H), 4.30(q, 2H), 7.07(d, 1H), 7.88(dd, 1H), 8.77(d, 1H) |
| 63 | methyl | propyl | ethyl | 1-ethyl-3-pyrrolidinyl methyl | 0.99(t, 3H), 1.10(t, 3H), 1.61(t, 3H), 1.82(m, 2H), 2.00(m, 1H), 2.50(m, 7H), 2.89(t, 2H), 2.90(m, 1H), 3.00(d, 2H), 4.25(s, 3H), 4.34(q, 2H), 7.10(d, 1H), 7.92(dd, 1H), 8.85(d, 1H) |
| 64 | methyl | propyl | propyl | 1-ethyl-3-pyrrollidinyl methyl | 0.98(t, 3H), 1.07(t, 3H), 1.15(t, 3H), 1.48(m, 1H), 1.82(m, 2H), 2.00(m, 3H), 2.40(m, 5H), 2.75(m, 1H), 2.87(t, 2H), 2.96(d, 2H), 4.21(q, 2H), 4.27(s, 3H), 7.09(d, 1H), 7.88(dd, 1H), 8.84(d, 1H) |
| 65 | ethyl | propyl | ethyl | 1-ethyl-3-pyrrolidinyl methyl | 0.99(t, 3H), 1.05(t, 3H), 1.48(t, 3H), 1.50(m, 1H), 1.62(t, 3H), 1.82(m, 2H), 1.95(m, 1H), 2.40(m, 6H), 2.80(m, 1H), 2.86(t, 2H), 2.92(d, 2H), 4.33(q, 2H), 4.61(q, 2H), 7.10(d, 1H), 7.91(dd, 1H), 8.87(d, 1H) |
| 66 | methyl | isobutyl | ethyl | 1-ethyl-3-pyrrolidinyl methyl | 0.94(d, 6H), 1.05(t, 3H), 1.50(m, 1H), 1.61(t, 3H), 1.93(m, 1H), 2.30(m, 7H), 2.80(d, 2H), 2.82(m, 1H), 2.99(d, 2H), 4.26(s, 3H), 4.34(q, 2H), 7.10(d, 1H), 7.91(dd, 1H), 8.86(d, 1H) |
| 67 | methyl | propyl | ethyl | 1-methyl-2-pyrrolidinyl ethyl | 1.02(t, 3H), 1.62(t, 3H), 1.85(m, 2H), 2.10(m, 8H), 2.79(s, 3H), 2.93(t, 2H), 3.18(m, 2H), 3.25(m, 1H), 3.65(m, 1H), 4.27(s, 3H), 4.35(q, 2H), 7.15(d, 1H), 8.00(dd, 1H), 8.86(d, 1H) |
| 68 | methyl | propyl | propyl | 1-methyl-2-pyrrolidinyl ethyl | 0.97(t, 3H), 1.16(t, 3H), 1.58(m, 4H), 1.80(m, 4H), 2.07(m, 3H), 2.28(s, 3H), 2.37(m, 1H), 2.93(t, 2H), 3.10(m, 3H), 4.22(q, 2H), 4.24(s, 3H), 7.11(d, 1H), 7.90(dd, 1H), 8.88(d, 1H) |
| 69 | ethyl | propyl | ethyl | 1-methyl-2-pyrrolidinyl ethyl | 1.02(t, 3H), 1.51(t, 3H), 1.61(m, 4H), 1.62(t, 3H), 1.86(m, 4H), 2.22(m, 1H), 2.36(s, 3H), 2.50(m, 1H), 2.93(t, 2H), 3.13(m, 3H), 4.36(q, 2H), 4.64(q, 2H), 7.12(d, 1H), 7.96(dd, 1H), 8.91(d, 1H) |
| 70 | methyl | isobutyl | ethyl | 1-methyl-2-pyrrolidinyl ethyl | 0.97(t, 3H), 1.50(m, 4H), 1.60(t, 3H), 1.78(m, 2H), 2.12(m, 2H), 2.28(s, 3H), 2.38(m, 1H), 2.80(d, 2H), 3.10(m, 3H), 4.26(s, 3H), 4.35(q, 2H), 7.10(d, 1H), 7.91(dd, 1H), 8.88(d, 1H) |

Experiment 1

Test for a Penile Erefection Using Rats

In order to confirm the efficacy on impotence of the compounds of formula 1, penile erection test was carried out with the normal rat model based on the methods of Benassi-Benelli et al. (*Arch. International de Pharmaco-dynamie et de Therapie.*, 1979, 242, 241–247), Islam et al. (*J. Ethnopharmacol.*, 1991, 33, 67–72) and Heaton et al. (*J. Urol.*, 1991, 145, 1099–1102).

Pyrazolopyrimidinone derivatives were suspended in 0.5% methyl cellulose and orally administered to rats with a single dose of 10 mg/kg/10 ml. After the administration of the drug, the rats were continously observed in terms of the number of penile erections and the number of genital groomings for 2 hours and the penile erection index (PEI) was calculated. The statistical significance of the differences between groups was calculated using Duncan's multiple comparison by the customary statistics program, Sigma-Stat$^R$. More than three rats were assigned to each group. To the rats of the other two groups were adminstered only the equivalent amount of 0.5% methyl cellulose or 10 mg/kg of sildenafil.citrate, and served as negative and positive control group, respectively.

The penile erection indices in rat model with pyrazolopyrimidinone derivatives of examples 1–70 are listed in the following table 2.

TABLE 2

| test group | PEI | genital grooming |
|---|---|---|
| control | 32.0 ± 23.1 | 3.8 ± 2.1 |
| 1 | 366.7 ± 38.5 | 3.0 ± 1.0 |
| 2 | 533.3 ± 305.5 | 5.7 ± 2.5 |
| 3 | 233.3 ± 152.8 | 2.7 ± 2.1 |
| 4 | 133.3 ± 57.7 | 2.3 ± 1.2 |
| 5 | 266.7 ± 57.7 | 3.3 ± 1.2 |
| 6 | 44.4 ± 38.5 | 1.3 ± 0.6 |
| 7 | 200.0 ± 0.0 | 6.7 ± 3.8 |
| 8 | 200.0 ± 100.0 | 3.0 ± 1.0 |
| 9 | 200.0 ± 100.0 | 4.7 ± 1.2 |
| 10 | 466.7 ± 305.5 | 4.0 ± 1.7 |
| 11 | 100 ± 0.0 | 2.7 ± 2.1 |
| 12 | 22.2 ± 38.5 | 0.3 ± 0.6 |
| 13 | 300.0 ± 100.0 | 4.3 ± 1.2 |
| 14 | 233.3 ± 57.7 | 3.0 ± 1.0 |
| 15 | 111.1 ± 101.8 | 0.7 ± 0.6 |
| 16 | 100 ± 0 | 1.7 ± 0.6 |
| 17 | 66.7 ± 66.7 | 1.0 ± 1.0 |
| 18 | 44.4 ± 38.5 | 1.3 ± 0.6 |
| 19 | 233.3 ± 57.7 | 5.0 ± 0.0 |
| 20 | 266.7 ± 57.7 | 2.3 ± 0.6 |
| 21 | 44.4 ± 38.5 | 2.3 ± 1.5 |
| 22 | 300.0 ± 200.0 | 2.7 ± 2.1 |
| 23 | 266.7 ± 57.7 | 3.0 ± 1.0 |
| 24 | 233.3 ± 230.9 | 2.7 ± 2.9 |
| 25 | 44.4 ± 38.5 | 2.0 ± 0.0 |
| 26 | 133.3 ± 133.3 | 4.0 ± 1.7 |
| 27 | 66.7 ± 66.7 | 2.7 ± 1.2 |
| 28 | 300.0 ± 100.0 | 3.0 ± 1.0 |
| 29 | 233.3 ± 152.8 | 3.0 ± 2.0 |
| 30 | 133.3 ± 57.7 | 2.3 ± 0.6 |
| 31 | 300.0 ± 0 | 3.3 ± 0.6 |
| 32 | 66.7 ± 66.7 | 1.3 ± 1.5 |
| 33 | 233.3 ± 57.7 | 2.7 ± 0.6 |
| 34 | 166.7 ± 57.7 | 1.3 ± 0.6 |
| 35 | 200.0 ± 0.0 | 2.0 ± 0.0 |
| 36 | 200.0 ± 173.2 | 1.3 ± 0.6 |
| 37 | 166.7 ± 57.7 | 1.3 ± 0.6 |
| 38 | 233.3 ± 230.9 | 2.7 ± 2.9 |
| 39 | 166.7 ± 57.7 | 1.3 ± 1.5 |
| 40 | 177.8 ± 203.7 | 1.7 ± 1.5 |
| 41 | 177.8 ± 203.7 | 1.7 ± 1.5 |
| 42 | 33.3 ± 57.7 | 1.3 ± 1.5 |
| 43 | 11.1 ± 19.3 | 0.7 ± 0.6 |
| 44 | 166.7 ± 115.5 | 1.3 ± 0.6 |
| 45 | 22.2 ± 38.5 | 0.7 ± 1.2 |
| 46 | 200.0 ± 173.2 | 1.3 ± 0.6 |
| 47 | 200.0 ± 100.0 | 3.0 ± 1.0 |
| 48 | 166.7 ± 57.7 | 1.3 ± 0.6 |
| 49 | 200.0 ± 173.2 | 1.3 ± 0.6 |
| 50 | 44.3 ± 38.5 | 1.0 ± 0.0 |

TABLE 2-continued

| test group | PEI | genital grooming |
|---|---|---|
| 51 | 233.3 ± 152.8 | 3.0 ± 2.0 |
| 52 | 233.3 ± 57.7 | 3.0 ± 1.0 |
| 53 | 300.0 ± 200.0 | 2.7 ± 2.1 |
| 54 | 233.3 ± 230.9 | 2.7 ± 2.9 |
| 55 | 350.0 ± 173.2 | 3.8 ± 1.5 |
| 56 | 200.0 ± 81.7 | 2.0 ± 0.0 |
| 57 | 131.3 ± 128.1 | 1.8 ± 1.3 |
| 58 | 275.0 ± 170.8 | 3.0 ± 1.8 |
| 59 | 150.0 ± 57.7 | 1.5 ± 0.6 |
| 60 | 300.0 ± 81.7 | 2.8 ± 0.5 |
| 61 | 25.0 ± 28.9 | 0.8 ± 0.5 |
| 62 | 200.0 ± 100.0 | 3.0 ± 1.0 |
| 63 | 12.5 ± 25.0 | 1.5 ± 0.6 |
| 64 | 175.0 ± 95.7 | 2.8 ± 0.5 |
| 65 | 93.8 ± 94.4 | 1.8 ± 1.0 |
| 66 | 175.0 ± 95.7 | 2.8 ± 0.5 |
| 67 | 75.0 ± 61.2 | 1.8 ± 1.5 |
| 68 | 233.3 ± 152.8 | 3.0 ± 2.0 |
| 69 | 225.0 ± 95.7 | 2.3 ± 1.0 |
| 70 | 175.0 ± 50.0 | 1.8 ± 0.5 |
| sildenafil | 200.0 ± 173.2 | 3.1 ± 1.2 |

As a result, the usefulness of the pyrazolopyrimidinone derivatives of the present invention was demonstrated by their higher penile erection index than sildenafil, presently used for the treatment of impotence by oral administration.

Experiment 2

Test for Phosphodiesterase-5 (PDE 5) Activity

In order to estimate the extent of inhibition for PDE 5 activity, of the compounds of formula 1, the following test was carried out.

Phosphodiesterase-5 enzyme (PDE 5) was separated from human corpus cavernosal tissues. About 3 g of this tissue was homogenized with 12 ml of Hepes buffer (20 mM Hepes, 250 mM Sucrose, 1 mM EDTA, 1 mM PMSF, pH 7.2) at 4° C. The solution was filtered with double-layered gauze and centrifuged (100,000×g) for 60 min at 4° C. The supernatant was filtered with 0.2 um filter paper and separated by HPLC (Mono Q anion exchange column) with concentration gradient of 0–500 mM NaCl to elute PDE isozymes. The enzyme activity was measured on the each column fraction by the following process to separate PDE 5 fraction and the inhibition for PDE 5 of the compounds of formula 1 was measured using the fraction.

To 1.5 ml tube were added 100 ul of reaction mixture (15 mM Tris-HCl, 5 mM $MgCl_2$, 0.5 mg/ml BSA, pH 7.4) and the appropriate amount of PDE 5 fraction and PDE inhibitor and the mixture was mixed well. To this solution was added [$^3$H]-cAMP or [$^3$H]-cGMP (500 nM, 2 uCi/ml), the mixture was reacted in the incubator of 30° C. for about 1 hour and the reaction was quenched by putting the tube into boiling water for about 45 seconds to 2 min. Then the tube was chilled in ice bath for about 5 min. To this tube was added snake venom (1 mg/ml, 100 ul) or 5'-nucleotidase (0.1 unit/tube) and the mixture was reacted in incubator of 37° C. for 10 min and chilled in ice bath. 3 times volume of methanol to the resin was added to the anion exchange resin (Bio-Rad resin, AG1-X2, 200–400 mesh) which had been already washed with 0.5 N HCl, $H_2O$, 0.5 N $NaOHH_2O$, 0.5 N HCl and $H_2O$ in order and adjusted to pH 5. Then 1 ml of the pretreated resin was dispensed into the each tube with vortexing. The mixture was left at 4° C. for 15 min with occasional vortexing and centrifuged (10,000 rpm) for about 15 min to sediment the resin. The supernatant (700 ul) was transferred to a liquid scintillation vial, and mixed with 10 ml of scintillation cocktail. After stabilizing the solution by leaving it overnight, the radioactivity of the tube was measured by β-counter.

TABLE 3

| test compound | $IC_{50}$ (ng/ml) | test compound | $IC_{50}$ (ng/ml) |
|---|---|---|---|
| sildenafil | 7.84 ± 0.32 | 9 | 4.78 ± 0.25 |
| 1 | 3.74 ± 0.11 | 10 | 1.69 ± 0.08 |
| 2 | 5.33 ± 0.09 | 13 | 9.35 ± 0.82 |
| 3 | 2.40 ± 0.32 | 14 | 35.4 ± 1.25 |
| 5 | 8.79 ± 0.59 | 19 | 2.36 ± 0.08 |
| 7 | 8.97 ± 0.67 | 22 | 6.78 ± 0.56 |
| 8 | 11.31 ± 0.98 | 23 | 6.31 ± 0.51 |
| 24 | 42.6 ± 1.52 | 52 | 4.91 ± 0.19 |
| 26 | 36.2 ± 0.98 | 53 | 10.23 ± 1.03 |
| 28 | 24.4 ± 1.25 | 54 | 19.12 ± 1.45 |
| 29 | 26.8 ± 0.78 | 55 | 50.57 ± 1.42 |
| 31 | 15.6 ± 0.85 | 56 | 7.13 ± 0.13 |
| 33 | 9.84 ± 0.23 | 57 | 16.74 ± 1.26 |
| 34 | 1.61 ± 0.07 | 58 | 8.02 ± 0.33 |
| 35 | 0.451 ± 0.01 | 59 | 68.29 ± 2.68 |
| 36 | 1.49 ± 0.05 | 60 | 17.44 ± 1.92 |
| 37 | 0.433 ± 0.02 | 61 | 47.19 ± 1.98 |
| 38 | 3.78 ± 0.09 | 62 | 20.95 ± 1.59 |
| 39 | 0.560 ± 0.01 | 63 | 49.38 ± 1.43 |
| 40 | 4.20 ± 0.06 | 64 | 15.88 ± 1.55 |
| 41 | 1.10 ± 0.05 | 65 | 38.48 ± 1.98 |
| 44 | 0.163 ± 0.01 | 66 | 18.52 ± 1.39 |
| 46 | 0.597 ± 0.02 | 67 | 31.67 ± 1.54 |
| 47 | 1.34 ± 0.09 | 68 | 4.57 ± 0.04 |
| 48 | 0.442 ± 0.011 | 69 | 16.49 ± 0.88 |
| 49 | 0.149 ± 0.008 | 70 | 10.50 ± 0.96 |
| 51 | 0.744 ± 0.008 | | |

As a result, it was demonstrated that the pyrazolopyrimidinone derivatives of the present invention inhibit the phosphodiesterase-5 activity in a concentration of 0.1–50 ng/ml ($IC_{50}$) and therefore show prominent efficacy on the treatment of impotence in oral administration.

Experiment 3

Test for Phosphodiesterase-6 (PDE 6) Activity

The inhibitor for PDE 5 is known to additionally inhibit PDE 6 distributed in retina, isozyme of PDE 5, and which causes visual disorders. Therefore in order to estimate the extent of inhibition for PDE 6, of the compounds of formula 1, the following test was carried out.

Phosphodiesterase-6 enzyme (PDE 6) was separated from the retina of bullfrogs. The retina was added to Ringer's solution (105 mM NaCl, 2.5 mM KCl, 2 mM $MgCl_2$, 1 mM $CaCl_2$, 5 mM Glucose, 5 mM $NaHCO_3$, 10 mM Hepes, pH 7.5–7.6) containing 6% Percoll and the solution was shaken. Then the cells were disrupted with syringe pressure and centrifuged (about 10,000 rpm) instantaneously to remove the pigment, and the resulting fraction was used as PDE 6 fraction.

10 ul of reaction mixture (20 mM Tris-HCl, 10 mM $MgCl_2$, 0.5 mg/ml BSA, pH7.5) was dispensed into each well of microplate, to which were added 10 ul of fraction of PDE 6 and 10 ul of PDE inhibitor and the solution was mixed well. 10 ul of trypsin (about 20–100 ug/ml) was added to the solution, the mixture was reacted in incubator of 4° C. for 1 hour to activate PDE 6 and the reaction was quenched by adding 10 ul of soybean trypsin inhibitor (6 times higher concentration to the trypsin used). To this mixture was added 10 ul of cyclic nucleotide (generally, 10 mM cGMP was added) and appropriate amount of snake venom or 5'-nucleotidase, and the mixture was reacted in incubator of 37° C. for 20 min. The inorganic phosphate produced by this reaction was measured in absorbance at 700–750 nm by adding 150 ul of molybdate solution (0.4N $H_2SO_4$, 0.2% ammonium molybdate, 2% sodiumdodesyl sulfate, 2% ascorbic acid) prepared immediately before.

TABLE 4

| test compound | IC$_{50}$ (ng/ml) | test compound | IC$_{50}$ (ng/ml) |
|---|---|---|---|
| sildenafil | 76.7 ± 1.53 | 22 | >1000 |
| 1 | 47.7 ± 1.56 | 23 | 330 ± 10.8 |
| 2 | >1000 | 24 | 583 ± 21.7 |
| 3 | 532 ± 23.6 | 26 | 243 ± 8.91 |
| 5 | 4.28 ± 0.14 | 28 | 250 ± 11.4 |
| 7 | 57.7 ± 1.25 | 29 | 813 ± 37.2 |
| 8 | 20.9 ± 1.56 | 31 | 44.3 ± 1.23 |
| 9 | 656 ± 25.8 | 33 | 608 ± 9.51 |
| 10 | 10.5 ± 0.56 | 34 | 27.4 ± 0.79 |
| 13 | 650 ± 28.4 | 35 | 29.1 ± 0.85 |
| 14 | 360 ± 12.3 | 36 | 6.04 ± 0.15 |
| 19 | 7.00 ± 0.09 | 37 | 3.41 ± 0.11 |
| 38 | 679 ± 31.7 | 57 | 119.7 ± 7.44 |
| 39 | 28.4 ± 1.0 | 58 | 56.1 ± 3.16 |
| 40 | 18.2 ± 0.77 | 59 | 168.9 ± 6.82 |
| 41 | 13.6 ± 0.81 | 60 | 41.0 ± 1.64 |
| 44 | 21.2 ± 1.59 | 61 | 53.3 ± 1.58 |
| 46 | 22.3 ± 0.98 | 62 | 75.9 ± 3.17 |
| 47 | 45.4 ± 1.46 | 63 | 65.8 ± 1.67 |
| 48 | 27.4 ± 1.73 | 64 | 48.9 ± 1.64 |
| 49 | 43.6 ± 2.45 | 65 | 58.9 ± 1.74 |
| 51 | 97.3 ± 2.46 | 66 | 44.6 ± 2.09 |
| 52 | >1000 | 67 | 163.0 ± 7.13 |
| 53 | 49.4 ± 1.39 | 68 | 126.9 ± 8.02 |
| 54 | 73.6 ± 1.19 | 69 | 57.5 ± 3.84 |
| 55 | >1000 | 70 | 85.7 ± 4.93 |
| 56 | 71.6 ± 1.85 | | |

As shown in the results, since the 50% inhibition concentration (IC$_{50}$) for PDE 6 is higher than for phosphodiesterase-5 in some of the pyrazolopyrimidinone derivatives, the probability of visual disorders caused by the compounds of the present invention can be much reduced compared with sildenafil.

Experiment 4

Test for Phosphodiesterase-3 (PDE 3) Activity

The inhibitor for PDE 5 may inhibit PDE 3 distributed in heart, isozyme of PDE 5, additionally, which may cause side effects in cardiovascular system. Therefore in order to estimate the extent of inhibition for PDE 3, of the compounds of formula 1, the following test was carried out.

Phosphodiesterase-3 enzyme (PDE 3) was separated from platelets of a rabbit. About 60 ml of blood was collected from a puncture of the abdominal artery of a rabbit in heparinized syringes. Platelet-rich plasma was harvested by centrifugation for 5 min at 450×g and further centrifuged for 15 min at 1,200×g to precipitate the platelets. The platelets were resuspended in homogenizing buffer (50 mM Tris-HCl, 1 mM $MgCl_2$, pH 7.4), homogenized at 4° C. and ultrasonicated (30 sec/ml). The homogenized solution was centrifuged (105,000×g) for 1 hr at 4° C. to obtain the supernatant in which PDE was dissolved. The supernatant was separated by DEAE-cellulose column chromatography (Whatman DE52 bead) by using eluent (50 mM Tris-HCl, 3.75mM2-mercaptoethanol, pH 6.0) with concentration gradient of 0–1 M sodium acetate to elute PDE isozymes. The PDE activity was measured on the each column fraction by the following process to separate PDE 3 fraction and the inhibition for PDE 3 of the compounds of formula 1 was measured by using the fraction.

To 1.5 ml tube containing 100 ul of reaction mixture (15 mM Tris-HCl, 5 mM $MgCl_2$, 0.5 mg/ml BSA, pH 7.4) were added appropriate amount of PDE 3 fraction and PDE inhibitor and the solution was mixed well. After [$^3$H]-cAMP or [$^3$H]-cGMP (500 nM, 2 uCi/ml) was added, the mixture was reacted in incubator of 30° C. for about 1 hour and the reaction was quenched by putting the tube into boiling water for about 45 seconds to 2 min. The tube was chilled in ice bath for about 5 min. To this tube was added snake venom (1 mg/ml, 100 ul) or 5'-nucleotidase (0.1 unit/tube) and the mixture was reacted in incubator of 37° C. for 10 min and chilled in ice bath. 3 times volume of methanol to the resin was added to the anion exchange resin (Bio-Rad resin, AG1-X2, 200–400 mesh) which had been already washed with 0.5 N HCl, $H_2O$, 0.5 N NaOH, $H_2O$, 0.5 N HCl and $H_2O$ in order and adjusted to pH 5. Then 1 ml of the pretreated resin was added to the each tube with vortexing. The mixture was left at 4° C. for 15 min with occasional vortexing and centrifuged (10,000 rpm) for about 5 min to sediment the resin. The supernatant (700 ul) was transferred to a liquid scintillation vial, and mixed with 10 ml of scintillation cocktail. After stabilizing the mixture by leaving it overnight, the radioactivity of the tube was measured by β-counter.

TABLE 5

| test compound | IC$_{50}$ (ug/ml) | test compound | IC$_{50}$ (ug/ml) |
|---|---|---|---|
| sildenafil | 33.9 ± 1.64 | 52 | >100 |
| 2 | >100 | 53 | >100 |
| 3 | >100 | 54 | >100 |
| 9 | >100 | 56 | >100 |
| 33 | 93.7 ± 0.54 | 57 | 24.0 ± 0.67 |
| 34 | 86.1 ± 0.21 | 58 | >100 |
| 35 | >100 | 59 | 59.8 ± 3.33 |
| 38 | 97.6 ± 0.09 | 60 | >100 |
| 39 | 20.1 ± 1.84 | 62 | 82.6 ± 2.41 |
| 41 | 4.79 ± 0.16 | 63 | 26.3 ± 1.06 |
| 44 | 6.27 ± 0.95 | 64 | 69.4 ± 2.64 |
| 46 | >100 | 65 | 16.6 ± 0.97 |
| 47 | 10.1 ± 0.56 | 66 | 46.7 ± 2.41 |
| 48 | 16.7 ± 1.52 | 68 | 36.2 ± 1.58 |
| 49 | 12.5 ± 0.78 | 69 | 39.5 ± 1.88 |
| 51 | >100 | 70 | 31.8 ± 1.21 |

As shown in the results, since the 50% inhibition concentration (IC$_{50}$) for PDE 3 is higher than for PDE 5 in some of the pyrazolopyrimidinone derivatives, the probability of side effects in cardiovascular system caused by the compounds of the present invention can be much reduced compared with sildenafil.

Experiment 5

Acute Oarl Toxicity Test in Rats

The test for confirming the toxicity of the compounds of formula 1 was carried out as follows.

In this test six-week old SPF SD rats were used, and two rats were assigned to each group. The compounds of examples 1, 2, 3, 5, 7, 8, 9, 10, 13, 14, 19, 22, 23, 24, 26, 28, 29, 31, 33, 34,35, 36, 37, 38, 39, 40, 41, 44, 46, 47, 48, 49, 51, 52, 53, 54, 56, 58, 60, 62, 64, 66, 68 and 70 were suspended in 0.5% methyl cellulose respectively, and administered orally with single dose of 1 g/kg using a ball-tipped needle. The dosing volume was 10 ml/kg. After the administration, the animals were observed for clinical signs of toxicity or mortality and the body weight changes were measured. All survivors at the end of the observation period underwent laparotomy under ether anesthesia and the blood samples were taken from the abdominal aorta for hematological tests and biochemical analysis. After sacrificing the animals, autopsy was performed for macroscopic observation of the organs and tissues. Tissue samples of vital organs from macroscopic legion were removed and fixed in 10% neutral buffered formalin solution, then processed by standard procedures for histopathology and examined with light microscope. There were no significant clinical symptoms, body weight changes and mortalities. Also in hematology, serum chemistry parameters and macroscopic observation, no drug-related changes were observed. As are sult all the compounds tested did not show toxicity in rats up to 1 g/kg, and the lethal dose ($LD_{50}$) of oral administration was determined to be over 1 g/kg in rats.

Experiment 6

Solubility in Buffer Solution in pH=2&5

In order to evaluate the solubilities in water of the compounds of formula 1 in pH=2 and 5 buffer solutions, the experiment as below was performed.

According to that defined in the Korea Pharmacopoeia, citrate-HCl buffer (pH 2) and citrate-NaOH buffer (pH 5) solutions were added to the powdered compounds of formula 1, respectively. After subsequent severe shaking for 30 sec every 5 min in 20_5° C. for 30 min, the level of compounds in the filtrate was measured by high performance liquid chromatography. The results were shown in Table 6.

TABLE 6

| test compound | solubility (ug/ml) | |
|---|---|---|
| | pH 2 | pH 5 |
| sildenafil | 1585 | 480 |
| 35 | 11 | 1 |
| 37 | 99 | 7 |
| 44 | 373 | 1 |
| 46 | 183 | 0.4 |
| 48 | 114 | 0.3 |
| 49 | 43 | 0 |
| 51 | 215 | 1 |
| 56 | 3918 | 6361 |
| 58 | 3722 | 9003 |
| 60 | 4497 | 4923 |
| 62 | 4383 | 3596 |
| 68 | 5356 | 14758 |
| 70 | 795 | 708 |

As shown in the results, the solubilities in water of the compounds according to the present invention are very high. The solubilities in water at pH 2 and 5 of sildenafil were 1585 and 480 ug/ml, respectively. On the other hand, the solubilities in water of the compounds of the present invention, preferably of exmaples 56, 58, 60, 62 and 68, were 3722–5356 and 4923–14758 ug/ml at pH 2 and 5, respectively. That is, the solubilities in water of the compounds according to the present invention has been increased to maximum 3.3 and 30.7 times compared with those of sildenafil at pH 2 and 5, respectively.

The solubility in water, in particular in acidic range of pH, of the compound is the very important factor determining the absorption of the compound in oral administration. Therefore, the better absorption of the compounds according to the present invention are expected in the light of the higher solubility of the compounds in acidic range of pH. Also they have an advantage of reducing the dose in oral administration.

Experiment 7

Metabolism in Rat Liver

In order to evaluate the extent of metabolism of the compounds of formula 1, the metabolism in rat liver was studied as below similar to the reported method (C. L. Litterist, E. G. Mimnaugh, R. I. Reagan and T. G. Gram., *Drug. Metabol. Disposit.*, 1975, 3, 259–265). In short, the disappearance of compounds after incubation in 9, 000×g supernatant fraction of rat liver homogenate in the presence of NADPH (reduced nicotinamide adenine dinucleotide phosphate) was evaluated.

First, Sprague-Dawley rat (Korea Experiment Animals, SPF) liver was isolated after perfusion through portal vein with 0.1 M phosphate buffer of pH 7.0 using tissue homogenizer at 4° C. After centrifugation at 9,000×g for 20 min, the supernatants were collected.

The compound stock solution was spiked (10 ug/ml) into each of the eppendorf tubes containing 1 ml of the mixed solution composing 1 volume of supernatants and 2 volumes of generating solution. The generating solution contains 1 mM NADP, 10 mM glucose-6-phosphate, 50 mM nicotinamide and 5 MM $MgCl_2$ in 0.1 M phosphate buffer of pH 7.0. After vortex-mixing, each test tube was incubated in a water bath kept at 37° C. After 1 hr, was added acetonitrile to the reaction mixture and centrifuged. 100 ul of aliquot of the supernatant was sampled from each test tube for measuring the remnants by high performance liquid chromatography. The results were shown in Table 7.

TABLE 7

| test compound | remnants (%) |
|---|---|
| sildenafil | 34.6 |
| 35 | 90.6 |
| 37 | 94.8 |
| 44 | 49.8 |
| 46 | 75.9 |
| 48 | 66.0 |
| 49 | 71.3 |
| 51 | 70.4 |
| 56 | 83.9 |
| 58 | 93.5 |
| 60 | 78.2 |
| 62 | 94.5 |
| 68 | 93.0 |
| 70 | 94.1 |

As shown in the results, the extent of metabolism of the compounds in rat liver is noticeably decreased. The remnant (%) of some of the compounds in liver was over 50% while that of sildenafil in liver was about 35%. In particular, the remnant (%) of some of the compounds of the present invention was over 80% and 95% at maximum. That is, it was confirmed that some of the compounds of the present invention were hardly metabolized in liver.

The level of metabolism of the compound in liver is another important factor determining the bioavailability and the in vivo effect, accompanied with the solubility in acidic conditions. The low remnant(%) requires the increase of the dose. Therefore the higher bioavailability and the better in vivo effect of the compounds of the present invention are expected in the light of the less metabolism in liver. Also the compounds of the present invention have an advantage of reducing the dose in oral administration.

What is claimed is:

1. A compound represented by the following formula (I) or a pharmaceutically acceptable salt thereof (formula not shown),

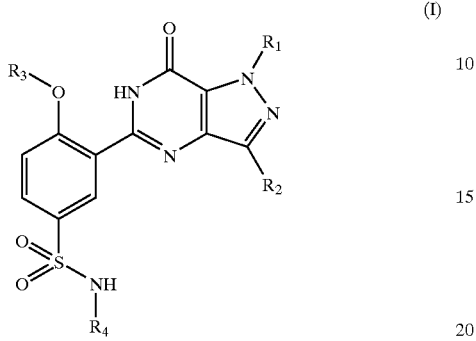

(I)

wherein $R_1$ is an alkyl group of $C_1$–$C_3$, $R_2$ is a substituted or unsubstituted alkyl group of $C_2$–$C_6$, $R_3$ is a substituted or unsubstituted alkyl group of $C_2$–$C_6$, and $R_4$ is a substituted or unsubstituted alkyl group of $C_1$–$C_6$, a substituted or unsubstituted cycloalkyl group of $C_3$–$C_6$, a substituted or unsubstituted benzene, a substituted or unsubstituted pyridine, or a substituted or unsubstituted pyrrole, wherein the substituent for the substituted groups is selected from the following group:

$C_1$–$C_{10}$-alkyl group, $C_3$–$C_6$ cycloalkyl, halogen, $C_1$–$C_6$ fluoroalkyl group, $C_1$–$C_{10}$ alkoxy group, substituted or unsubstituted benzene or heterocycle, wherein the heterocycle is selected from the group consisting of pyridine, isoxazole, thiazole, pyrimidine, indan, benzthiazole, pyrazole, thiadiazole, oxazole, piperidine, morpholine, imidazole, pyrrolidine, thienyl, triazole, pyrrol and furyl.

2. The compound according to claim 1, wherein $R_4$ is a substituted alkyl group of $C_1$–$C_6$ and the substituent is pyrrolidine.

3. The compound according to claim 1, which is selected from the group consisting of:

5-[2-ethoxy-5-(isopropylamidosulfonyl)phenyl]-1-methyl-3-propyl-1,6-dihydro-7H-pyrazolo(4,3-d)pyrimidin-7-one;

5-[2-ethoxy-5-(benzylamidosulfonyl)phenyl]-1-methyl-3-isobutyl-1,6-dihydro-7H-pyrazolo(4,3-d)pyrimidin-7-one;

5-[2-propyloxy-5-(isopropylamidosulfonyl)phenyl]-1-methyl-3-propyl-1,6-dihydro-7H-pyrazolo(4,3-d)pyrimidin-7-one;

5-[2-ethoxy-5-(butylamidosulfonyl)phenyl]-1-methyl-3-propyl-1,6-dihydro-7H-pyrazolo(4,3-d)pyrimidin-7-one;

5-[2-ethoxy-5-(cyclopropylamidosulfonyl)phenyl]-1-methyl-3-propyl-1,6-dihydro-7H-pyrazolo(4,3-d)pyrimidin-7-one;

5-[2-ethoxy-5-(benzylamidosulfonyl)phenyl]-1-methyl-3-propyl-1,6-dihydro-7H-pyrazolo(4,3-d)pyrimidin-7-one;

5-[2-propyloxy-5-(benzylamidosulfonyl)phenyl]-1-methyl-3-propyl-1,6-dihydro-7H-pyrazolo(4,3-d)pyrimidin-7-one;

5-[2-ethoxy-5-(4-fluorophenylamidosulfonyl)phenyl]-1-ethyl-3-propyl-1,6-dihydro-7H-pyrazolo(4,3-d)pyrimidin-7-one;

5-[2-ethoxy-5-(4-pyridylamidosulfonyl)phenyl]-1-methyl-3-propyl-1,6-dihydro-7H-pyrazolo(4,3-d)pyrimidin-7-one;

5-[2-propyloxy-5-(4-pyridylamidosulfonyl)phenyl]-1-methyl-3-propyl-1,6-dihydro-7H-pyrazolo(4,3-d)pyrimidin-7-one;

5-[2-ethoxy-5-(4-pyridylamidosulfonyl)phenyl]-1-ethyl-3-propyl-1,6-dihydro-7H-pyrazolo(4,3-d)pyrimidin-7-one;

5-[2-ethoxy-5-(4-pyridylamidosulfonyl)phenyl]-1-methyl-3-isobutyl-1,6-dihydro-7H-pyrazolo(4,3-d)pyrimidin-7-one;

5-[2-ethoxy-5-(3-pyridylamidosulfonyl)phenyl]-1-methyl-3-propyl-1,6-dihydro-7H-pyrazolo(4,3-d)pyrimidin-7-one;

5-[2-propyloxy-5-(3-pyridylamidosulfonyl)phenyl]-1-methyl-3-propyl-1,6-dihydro-7H-pyrazolo(4,3-d)pyrimidin-7-one;

5-[2-ethoxy-5-(3-pyridylamidosulfonyl)phenyl]-1-ethyl-3-propyl-1,6-dihydro-7H-pyrazolo(4,3-d)pyrimidin-7-one;

5-[2-ethoxy-5-(3-pyridylamidosulfonyl)phenyl]-1-methyl-3-isobutyl-1,6-dihydro-7H-pyrazolo(4,3-d)pyrimidin-7-one;

5-[2-propyloxy-5-(4-pyridylmethylamidosulfonyl)phenyl]-1-methyl-3-propyl-1,6-dihydro-7H-pyrazolo(4,3-d)pyrimidin-7-one;

5-[2-ethoxy-5-(4-pyridylmethylamidosulfonyl)phenyl]-1-methyl-3-isobutyl-1,6-dihydro-7H-pyrazolo (4,3-d)pyrimidin-7-one;

5-[2-ethoxy-5-(3-pyridylmethylamidosulfonyl)phenyl]-1-methyl-3-propyl-1,6-dihydro-7H-pyrazolo(4,3-d)pyrimidin-7-one;

5-[2-ethoxy-5-(3-pyridylmethylamidosulfonyl)phenyl]-1-methyl-3-isobutyl-1,6-dihydro-7H-pyrazolo(4,3-d)pyrimidin-7-one;

5-[2-propyloxy-5-(3-pyridylmethylamidosulfonyl)phenyl]-1-methyl-3-propyl-1,6-dihydro-7H-pyrazolo (4,3-d)pyrimidin-7-one;

5-[2-ethoxy-5-(2-pyridylmethylamidosulfonyl)phenyl]-1-methyl-3-isobutyl-1,6-dihydro-7H-pyrazolo(4,3-d)pyrimidin-7-one;

5-[2-propyloxy-5-(2-pyridylmethylamidosulfonyl)phenyl]-1-methyl-3-propyl-1,6-dihydro-7H-pyrazolo (4,3-d)pyrimidin-7-one;

5-[2-propyloxy-5-(1-methyl-2-pyrrolidinylmethylamidosulfonyl)phenyl]-1-methyl-3-propyl-1,6-dihydro-7H-pyrazolo(4,3-d)pyrimidin-7-one;

5-[2-ethoxy-5-(1-methyl-2-pyrrolidinylmethylamidosulfonyl)phenyl]-1-methyl-3-isobutyl-1,6-dihydro-7H-pyrazolo(4,3-d)pyrimidin-7-one;

5-[2-propyloxy-5-(1-methyl-3-pyrrolidinylmethylamidosulfonyl)phenyl]-1-methyl-3-propyl-1,6-dihydro-7H-pyrazolo(4,3-d)pyrimidin-7-one;

5-[2-ethoxy-5-(1-methyl-3-pyrrolidinylmethylamidosulfonyl)phenyl]-1-methyl-3-isobutyl-1,6-dihydro-7H-pyrazolo(4,3-d)pyrimidin-7-one; and, 5-[2-propyloxy-5-(1-methyl-2-pyrrolidinylethylamidosulfonyl)phenyl]-1-methyl-3-propyl-1,6-dihydro-7H-pyrazolo(4,3-d)pyrimidin-7-one, 4. The compound according to claim 3, which is selected from the group consisting of:

5-[2-ethoxy-5-(4-pyridylamidosulfonyl)phenyl]-1-methyl-3-propyl-1,6-dihydro-7H-pyrazolo(4,3-d)pyrimidin-7-one;

5-[2-propyloxy-5-(4-pyridylamidosulfonyl)phenyl]-1-methyl-3-propyl-1,6-dihydro-7H-pyrazolo(4,3-d)pyrimidin-7-one;

5-[2-ethoxy-5-(4-pyridylamidosulfonyl)phenyl]-1-ethyl-3-propyl-1,6-dihydro-7H-pyrazolo(4,3-d)pyrimidin-7-one;

5-[2-ethoxy-5-(4-pyridylamidosulfonyl)phenyl]-1-methyl-3-isobutyl-1,6-dihydro-7H-pyrazolo(4,3-d)pyrimidin-7-one;

5-[2-ethoxy-5-(3-pyridylamidosulfonyl)phenyl]-1-methyl-3-propyl-1,6-dihydro-7H-pyrazolo(4,3-d)pyrimidin-7-one;

5-[2-propyloxy-5-(3-pyridylamidosulfonyl)phenyl]-1-methyl-3-propyl-1,6-dihydro-7H-pyrazolo(4,3-d)pyrimidin-7-one;

5-[2-ethoxy-5-(3-pyridylamidosulfonyl)phenyl]-1-ethyl-3-propyl-1,6-dihydro-7H-pyrazolo(4,3-d)pyrimidin-7-one;

5-[2-ethoxy-5-(3-pyridylamidosulfonyl)phenyl]-1-methyl-3-isobutyl-1,6-dihydro-7H-pyrazolo(4,3-d)pyrimidin-7-one;

5-[2-propyloxy-5-(4-pyridylmethylamidosulfonyl)phenyl]-1-methyl-3-propyl-1,6-dihydro-7H-pyrazolo(4,3-d)pyrimidin-7-one;

5-[2-ethoxy-5-(4-pyridylmethylamidosulfonyl)phenyl]-1-methyl-3-isobutyl-1,6-dihydro-7H-pyrazolo (4,3-d)pyrimidin-7-one;

5-[2-ethoxy-5-(3-pyridylmethylamidosulfonyl)phenyl]-1-methyl-3-propyl-1,6-dihydro-7H-pyrazolo(4,3-d)pyrimidin-7-one;

5-[2-ethoxy-5-(3-pyridylmethylamidosulfonyl)phenyl]-1-methyl-3-isobutyl-1,6-dihydro-7H-pyrazolo(4,3-d)pyrimidin-7-one;

5-[2-propyloxy-5-(3-pyridylmethylamidosulfonyl)phenyl]-1-methyl-3-propyl-1,6-dihydro-7H-pyrazolo(4,3-d)pyrimidin-7-one;

5-[2-ethoxy-5-(2-pyridylmethylamidosulfonyl)phenyl]-1-methyl-3-isobutyl-1,6-dihydro-7H-pyrazolo(4,3-d)pyrimidin-7-one;

5-[2-propyloxy-5-(2-pyridylmethylamidosulfonyl)phenyl]-1-methyl-3-propyl-1,6-dihydro-7H-pyrazolo(4,3-d)pyrimidin-7-one;

5-[2-propyloxy-5-(1-methyl-2-pyrrolidinylmethylamidosulfonyl)phenyl]-1-methyl-3-propyl-1,6-dihydro-7H-pyrazolo(4,3-d)pyrimidin-7-one;

5-[2-ethoxy-5-(1-methyl-2-pyrrolidinylmethylamidosulfonyl)phenyl]-1-methyl-3-isobutyl-1,6-dihydro-7H-pyrazolo(4,3-d)pyrimidin-7-one;

5-[2-propyloxy-5-(1-methyl-3-pyrrolidinylmethylamidosulfonyl)phenyl]-1-methyl-3-propyl-1,6-dihydro-7H-pyrazolo(4,3-d)pyrimidin-7-one;

5-[2-ethoxy-5-(1-methyl-3-pyrrolidinylmethylamidosulfonyl)phenyl]-1-methyl-3-isobutyl-1,6-dihydro-7H-pyrazolo(4,3-d)pyrimidin-7-one; and, 5-[2-propyloxy-5-(1-methyl-2-pyrrolidinylethylamidosulfonyl)phenyl]-1-methyl-3-propyl-1,6-dihydro-7H-pyrazolo(4,3-d)pyrimidin-7-one;

5. The compound according to claim 4, which is selected from the group consisting of:

5-[2-propyloxy-5-(1-methyl-2-pyrrolidinylmethylamidosulfonyl)phenyl]-1-methyl-3-propyl-1,6-dihydro-7H-pyrazolo(4,3-d)pyrimidin-7-one;

5-[2-ethoxy-5-(1-methyl-2-pyrrolidinylmethylamidosulfonyl)phenyl]-1-methyl-3-isobutyl-1,6-dihydro-7H-pyrazolo(4,3-d)pyrimidin-7-one;

5-[2-propyloxy-5-(1-methyl-3-pyrrolidinylmethylamidosulfonyl)phenyl]-1-methyl-3-propyl-1,6-dihydro-7H-pyrazolo(4,3-d)pyrimidin-7-one;

5-[2-ethoxy-5-(1-methyl-3-pyrrolidinylmethylamidosulfonyl)phenyl]-1-methyl-3-isobutyl-1,6-dihydro-7H-pyrazolo(4,3-d)pyrimidin-7-one; and 5-[2-propyloxy-5-(1-methyl-2-pyrrolidinylethylamidosulfonyl)phenyl]-1-methyl-3-propyl-1,6-dihydro-7H-pyrazolo(4,3-d)pyrimidin-7-one.

6. The compound according to claim 5, which is 5-[2-propyloxy-5-(1-methyl-2-pyrrolidinylethylamidosulfonyl)phenyl]-1-methyl-3-propyl-1,6-dihydro-7H-pyrazolo(4,3-d)pyrimidin-7-one.

7. A method of treating for impotence by administering the compound according to any one of claims 1–6 or a pharmaceutically acceptable salt thereof as an active ingredient.

8. The method according to claim 7, further containing at least one pharmaceutically acceptable exceipient.

9. The method according to claim 7, wherein the compound is 5-[2-propyloxy-5-(1-methyl-2-pyrrolidinylethylamidosulfonyl)phenyl]-1-methyl-3-propyl-1,6-dihydro-7H-pyrozolo(4,3-d)pyrimidin-7-one).

10. The method according to claim 8, wherein the compound is 5-[2-propyloxy-5-(1-methyl-2-pyrrolidinylethylamidosulfonyl)phenyl]-1-methyl-3-propyl-1,6-dihydro-7H-pyrozolo(4,3-d)pyrimidin-7-one).

* * * * *